United States Patent [19]

McKinley et al.

[11] Patent Number: 5,408,882

[45] Date of Patent: Apr. 25, 1995

[54] ULTRASONIC DEVICE AND METHOD FOR NON-DESTRUCTIVE EVALUATION OF POLYMER COMPOSITES

[75] Inventors: Barbara J. McKinley, Castleton; Dean S. Matsumoto, Niskayuna; Robert S. Gilmore, Burnt Hills, all of N.Y.; Kevin P. McAlea, Austin, Tex.

[73] Assignee: General Electric Company, Schenectady, N.Y.

[21] Appl. No.: 95,638

[22] Filed: Jul. 21, 1993

Related U.S. Application Data

[63] Continuation-in-part of Ser. No. 721,841, Jun. 24, 1991, abandoned.

[51] Int. Cl.⁶ ............................................. G01N 29/18
[52] U.S. Cl. ........................................ 73/597; 73/602; 73/644; 73/642
[58] Field of Search ................. 73/597, 599, 598, 602, 73/644, 642; 364/550, 551.01

[56] References Cited

U.S. PATENT DOCUMENTS

| | | | |
|---|---|---|---|
| 3,720,098 | 3/1973 | Dixon | 73/597 |
| 5,038,787 | 8/1991 | Antich et al. | 73/602 |
| 5,048,340 | 9/1991 | Thompson et al. | 73/597 |
| 5,127,268 | 7/1992 | Kline | 73/597 |

OTHER PUBLICATIONS

Composites, 20, 575–583 (1989).
Metallurgical Transactions A, 18A, 473–480 (1987).

Primary Examiner—Thomas P. Noland
Assistant Examiner—Nashmiya Ashraf
Attorney, Agent, or Firm—David C. Goldman; Paul R. Webb, II

[57] ABSTRACT

An ultrasonic measurement device and a method for a non-destructive evaluation of polymer composites having discontinuous fibers distributed therein. The device has one or a plurality of substantially matched pairs of transducers disposed on wedge shaped focuser and a relay, the focuser and relay each have their impedances substantially matched to that of the polymer composite being analyzed. The device is placed on a surface of the composite with the apexes of the focuser and relay in close contact with the surface. A velocity of a substantially longitudinal ultrasonic wave generated by the first transducer and received by the second transducer after its passage through the composite is determined at several angles of orientations about a center point, and the measured velocities of the ultrasonic wave are processed through a computer having software to determine the physical attributes of the composite, such as weight percentage of fibers present in the composite, Young's modulus, shear modulus and Poisson's ratio of the composite.

26 Claims, 20 Drawing Sheets

ULTRASONIC DEVICE AND METHOD FOR NON-DESTRUCTIVE EVALUATION OF POLYMER COMPOSITES

CROSS-REFERENCE TO RELATED APPLICATION

This application is a continuation-in-part of application Ser. No. 07/721,841 filed Jun. 24, 1991, now abandoned.

FIELD OF THE INVENTION

The present invention generally relates to an ultrasonic nondestructive measurement device and to a method of analyzing an attenuated ultrasonic wave transmitted through an interior of a medium under observation by measuring the acoustic characteristics of the interior. More particularly, the invention relates to an in-plane ultrasonic wave velocity measurement device and method for determining physical properties of a randomly distributed fiber reinforced polymer composite substrate.

BACKGROUND OF THE INVENTION

The acoustical spectrum may be divided into three regions on the basis of the limits of hearing of the human ear. The region from 20 to 20,000 cycles per second is generally referred to as the sonic, the region below 20 cycles per second is the infrasonic, and the region above 20,000 cycles per second as the ultrasonic region.

Non-destructive testing and evaluation is one of the most important fields of passive applications of ultrasonics. In ultrasound material testing, measuring the velocity of an attenuated wave in an object under an examination is one of the most useful expedients for determining the physical and material properties of the object.

Even though ultrasonics has been extensively used in metallurgy for detecting flaws and monitoring thickness of metal objects; its application to a nondestructive examination (hereinafter NDE) of polymers has been limited. There are several reasons for the lack of wide scale acceptance of NDE ultrasonic methods. Firstly, the attenuation of ultrasonic signals in polymers is, in general, several orders of magnitude larger than that typically found in metals. Adaptation of existing NDE methods for the study of polymers is feasible but such an adaptation requires a sufficient demand for the development of special high power ultrasonic generators and ultra sensitive ultrasonic wave detection systems to make ultrasonic measurements feasible. Secondly, the type of data generated by the NDE ultrasonic method is not widely understood and hence potential problems associated with NDE are generally not recognized. Finally, the generally low cost of polymeric articles makes routine examination of such articles economically not feasible. As a result, there was little desire to develop such methods. However, in recent years, the advent of specialty polymers has led to the use of polymers in large structural applications and, hence, there is now a justification to take a new look at non-destructive testing methods in general and to the ultrasonic techniques in particular.

An ultrasonic wave may be used to determine the physical attributes such as Young's modulus, Poisson's ratio, shear modulus and volumetric fraction of fiber reinforcement present in the fiber reinforced polymer composites.

When any type of reinforcement, such as nonrandomized discontinuous fibers, is present in the composite medium, such a medium exhibits anisotropic behavior. Anisotropic behavior results in a medium having properties that differ according to the direction of measurement, whereas isotropic behavior results in a medium having properties that are identical in all directions. Such isotropic behavior is typically exhibited by a composite medium having a substantially randomized three dimensional discontinuous fiber distribution.

As their name implies, fiber reinforced composite materials (also known simply as "composites") comprise fibers of materials such as carbon, boron, graphite, glass, nylon, polyester or metals and their alloys such as steel, impregnated with a matrix or a polymer material such as epoxy resin. Such composites typically exhibit extremely high strength to weight ratios, and accordingly their use is becoming increasingly popular in the aerospace and automotive industry.

One of the problems still associated with discontinuous fiber composites is anisotropic flow behavior. As a result, knowing the fiber orientation within composites allows one to predict an optimal direction in which the best mechanical properties may be obtained.

Still another problem especially associated with discontinuous randomly distributed fiber reinforced composites is that it is difficult to determine the volumetric fraction occupied by the fibers in a composite matrix to a degree of certainty typically desired in a manufacturing process. Accordingly, new means are constantly being sought for determining the fiber orientation and volumetric fraction more efficiently and at a lower cost.

Discontinuous fiber composites with long (typically about 0.5 to about 1.0 inch length) fibers such as glass fibers are being used in many applications where stiffness, impact strength, and low costs are important. An example of a discontinuous glass fiber composite is sheet molding compound (SMC) which contains a thermosetting resin, glass fiber and filler. The glass fiber may be in the form of a randomly distributed planar discontinuous fiber or a woven fiber mat or a continuous fiber. Composites based on a thermoplastic resin are also available. Examples of such thermoplastic composites are those produced by a process involving a powdered resin, chopped glass fibers, water and a surfactant mixed to form an aqueous foam. The foam is poured on a filter screen where water is removed by vacuum, leaving behind a fibrous web or felt of chopped fibers and resin particles. The web is then laminated under heat and pressure to form a sheet. Such sheets are then workformed into desired articles. The term "workforming" is defined as a method by which the aforementioned sheet may be shaped, machined, or modified in a predetermined manner. A workforming apparatus, such as a thermostamping machine, is well known in the art.

Discontinuous fiber composites of this type may be produced by either a batch or a continuous process. The batch process can be manipulated to produce felts with either some degree of in-plane fiber orientation or a nearly two dimensional random fiber distribution. In the continuous process of this type, the aqueous foam is fed through a manifold onto a moving filter screen, which may result in some preferred orientation in the direction of the moving filter screen. Such preferred orientation may be controlled by modifying the manifold design and adjusting the process variables, such as filter screen speed and flow rate of the aqueous foam. The fiber orientation in the sheet results in anisotropic flow behavior. For example, FIG. 1 shows the effect of fiber orientation on the deformation behavior of a test sample made of 30% by weight of glass filled polypropylene. "A" of FIG. 1 shows the original shape of a test sample, an arrow indicating the direction of the fiber orientation, and "B" of FIG. 1 shows the test sample after its compression to 60% of original thickness when pressed between the parallel plates of a squeeze flow rheometer. As seen in "B", a significantly larger deformation occurs in a direction orthogonal to the direction of the fiber orientation.

Such flow anisotropy complicates the selection of thermoforming molding conditions and placement of a blank in the thermoforming mold. In addition, anisotropy in final parts can lead to unbalanced residual stresses that may be sufficient to warp the thermoformed articles. Such anisotropic behavior is not always undesirable; but if controlled and understood, it can lead to a better and more efficient thermoforming process. Hence, there is a need for simple nondestructive, quantitative techniques for characterizing material anisotropy and mechanical properties in these composites.

An ultrasonic wave propagating through a solid body can be used as a probe for finding material alterations throughout that body. The use of such a probe offers a distinct advantage over techniques that rely on surface measurements of the body, since many properties exhibited by the surface layer of the body are not identical with the behavior exhibited by the bulk material of the body. Ultrasonic material evaluation techniques have been used for elastic property characterization of both isotropic and anisotropic materials. Ultrasonic methods for the testing of polymers have been developed using liquid immersion techniques, solid buffer rod techniques or direct contact techniques.

Ultrasonic immersion techniques are well known in the art and such techniques involve placing a sample in the path of a sound wave between a transmitting transducer and an opposite receiving transducer both of which are immersed in a sound conducting fluid. Under certain conditions mostly a longitudinal wave may be generated by changing the orientation of the sample with respect to a path of a sound wave (when the sound wave is perpendicular to the plane of the sample) or mostly a shear wave may be generated when the angle of incidence exceeds a critical value for total internal reflection (based on Snell's Law). The shear wave is also called a transverse wave.

The immersion technique suffers from several drawbacks. As can be seen in U.S. Pat. No. 4,346,599, to McLaughlen et al, the apparatus requires a great number of mechanical and moving parts (e.g., motors, gears, chains, cams, etc.) which demand minute adjustments. Furthermore, before any measurements can be made, fine adjustments must be made to the components of the apparatus. Such adjustments are difficult to make and can lead to erroneous results if not performed properly. As such they constitute a source of measurement error. Also, in the immersion technique it is necessary to perform all measurements in a water tank and a complicated numerical analysis procedure is needed for modulus determination.

Ultrasonic material evaluation techniques based on solid buffer rod techniques are well known. In such techniques the sample is placed between two solid (metal or glass) rods. A first transducer acting as a transmitter is affixed to a free end of the first buffer rod and a second transducer acting as a receiver is attached to a free end of the second buffer rod. An ultrasound burst is generated by the first transducer which then travels through the first rod, the sample, the second rod, and finally to the receiver. A part of the energy of the ultrasonic burst is transmitted through the sample and then received by the receiver where it is detected. However, such techniques are unsuitable for determining the in-plane properties of the sample under analysis.

In still another method, the velocity of plate bending (Lamb) waves is measured from a single side of the sample using a contacting transducer assembly. However, a fairly accurate estimate of the composite Poisson's ratio is needed to calculate the moduli. The aforementioned method was limited to determinations of the elastic moduli along the principal fiber directions in composites containing unidirectional and crossply geometries. An additional limitation of this method is the necessity of solving complex mathematical equations, such as the Fourier transforms of stored pulse wave forms, due to a dispersive nature of the Lamb waves.

Finally, most of the aforementioned prior art methods for the determination of elastic moduli require prior knowledge of the sample density, which is not usually known in the fiber reinforced composites.

SUMMARY OF THE INVENTION

The present invention is directed to a measurement device for determining in-plane physical attributes of an anisotropic lossy medium comprising wave generator means for generating an ultrasonic sound wave, focusing means having an impedance substantially matched to that of the medium whereby the focusing means focuses and transmits the ultrasonic wave through the medium, wave converter means for converting into an electrical signal a first attenuated wave received through the medium, relaying means having an impedance substantially matched to that of the medium wherein the relaying means relays the first attenuated wave to the converter means and processing means for transforming the signal into a display of the attributes.

A lossy medium is defined as a medium that appreciably dissipates energy, such as an ultrasonic wave, during transmission of the energy through the medium. The in-plane physical attributes of an anisotropic Lossy medium are defined as physical properties such as density, Young's modulus, Poisson's ratio or shear modulus of the medium.

The present invention is also directed to a method of determining the in-plane physical attributes of an anisotropic medium comprising:

selecting a surface area of the medium and placing a measurement device on the surface;

recording an angle of orientation ($\Psi$) of the device with respect to a datum;

transmitting an ultrasonic wave through the medium, determining the amplitude of a first attenuated ultrasonic wave;

matching said amplitude with a predetermined acceptable range;

determining a time interval required at the angle of orientation for the signal to arrive from the apex of the focusing means to the apex of the relaying means;

pivoting the device along its center point to place the device at a series of orientations for obtaining a corresponding series of time intervals, plotting a measured velocity distribution diagram as a function of the angle of orientation from $$v_m = \frac{s}{t}$$

where $v_m$ is the measured anisotropic velocity of the first attenuated ultrasonic wave through the medium, S is the distance between the apex of the focusing means and the apex of the relaying means, and t is the time interval;

screening the measured anisotropic velocity distribution diagram to determine a $v_{maximum}$, a $\Psi_{maximum}$, a $v_{minimum}$ and a $\Psi_{minimum}$;

computing a measured degree of anisotropy from $v_{minimum}/v_{maximum}$;

computing an area of the measured anisotropic velocity distribution diagram from $$\int_0^{2\pi} [v(\psi)]^2 d\psi/2$$

where $\pi$ equals 3.14159 . . .;

retrieving a lookup chart for the measured degree of anisotropy stored in a data storage area of the processing means wherein the lookup chart provides a measured normalized area distribution;

determining an area of isotropic velocity distribution from the measured anisotropic velocity distribution divided by the measured normalized area distribution, retrieving a lookup table for the area of measured isotropic velocity distribution stored in the data storage area of the processing means wherein the lookup table provides a measured volume fraction of the reinforcement present in the medium;

comparing and matching a theoretical velocity distribution diagram with the measured velocity distribution diagram to determine the eccentricity of an elliptical distribution function;

determining $C_{ijkl}$ tensors from the elliptical distribution function;

calculating the physical attributes of the medium from the $C_{ijkl}$ tensors; and displaying said attributes.

DETAILED DESCRIPTION OF THE PREFERRED EMBODIMENTS

Prior to discussing in detail the construction of the device of the preferred embodiments of the present invention, and the preferred methods of the present invention employing such devices, it is believed that the understanding of the invention by those skilled in the art will be aided by providing a discussion of the underlying concepts of the invention. Stated briefly, the device and method of the present invention were developed based upon the realization that it is possible to determine or measure the volume fraction of reinforcing fibers and the elastic properties in a predetermined area of a fiber reinforced composite material by making a plurality of ultrasonic wave velocity measurements across that area, as will be explained in more detail below.

Figure 1:
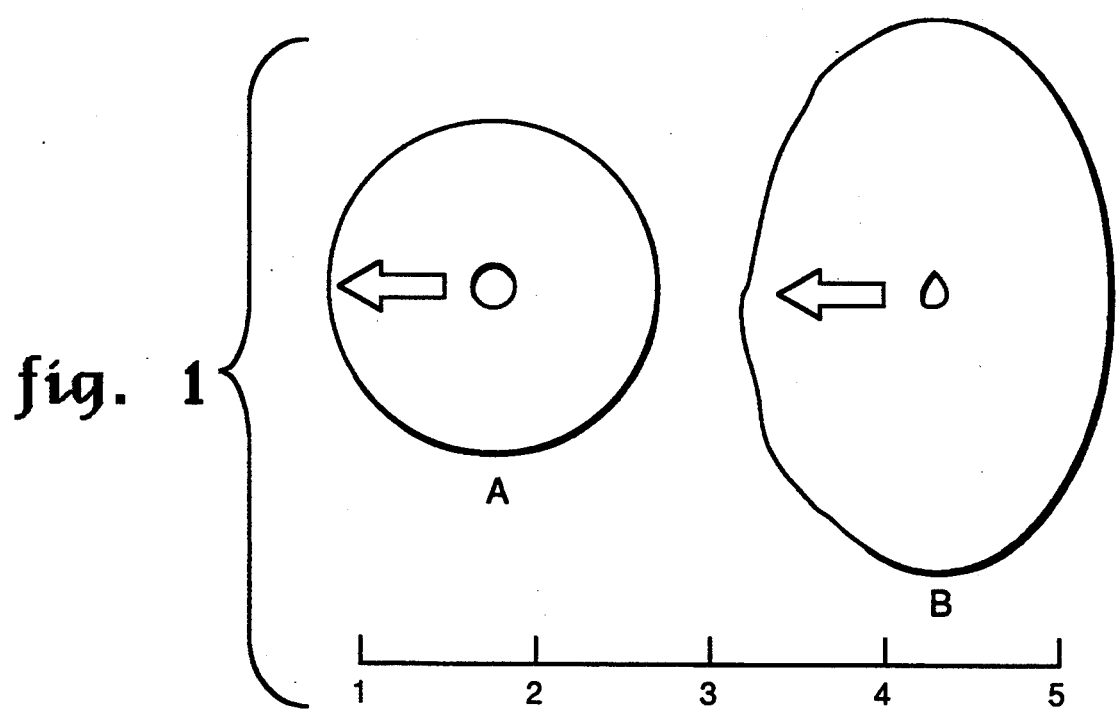
FIG. 1 illustrates an effect of the in-plane fiber orientation on the deformation characteristic of a test sample having fibers oriented in the direction of an arrow.
Figure 2:
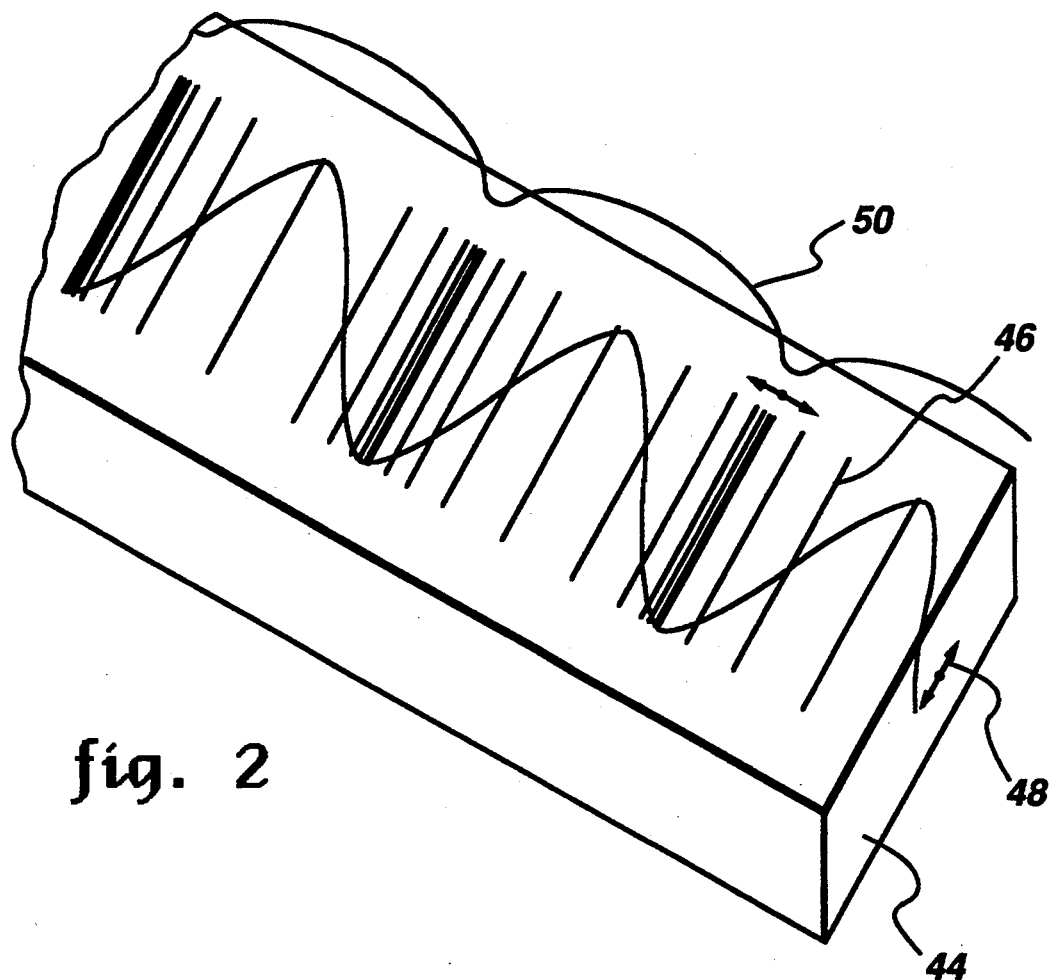
FIG. 2 provides a pictorial rendition of the various waves generated in a medium when an ultrasonic wave is transmitted through it.
Figure 4:
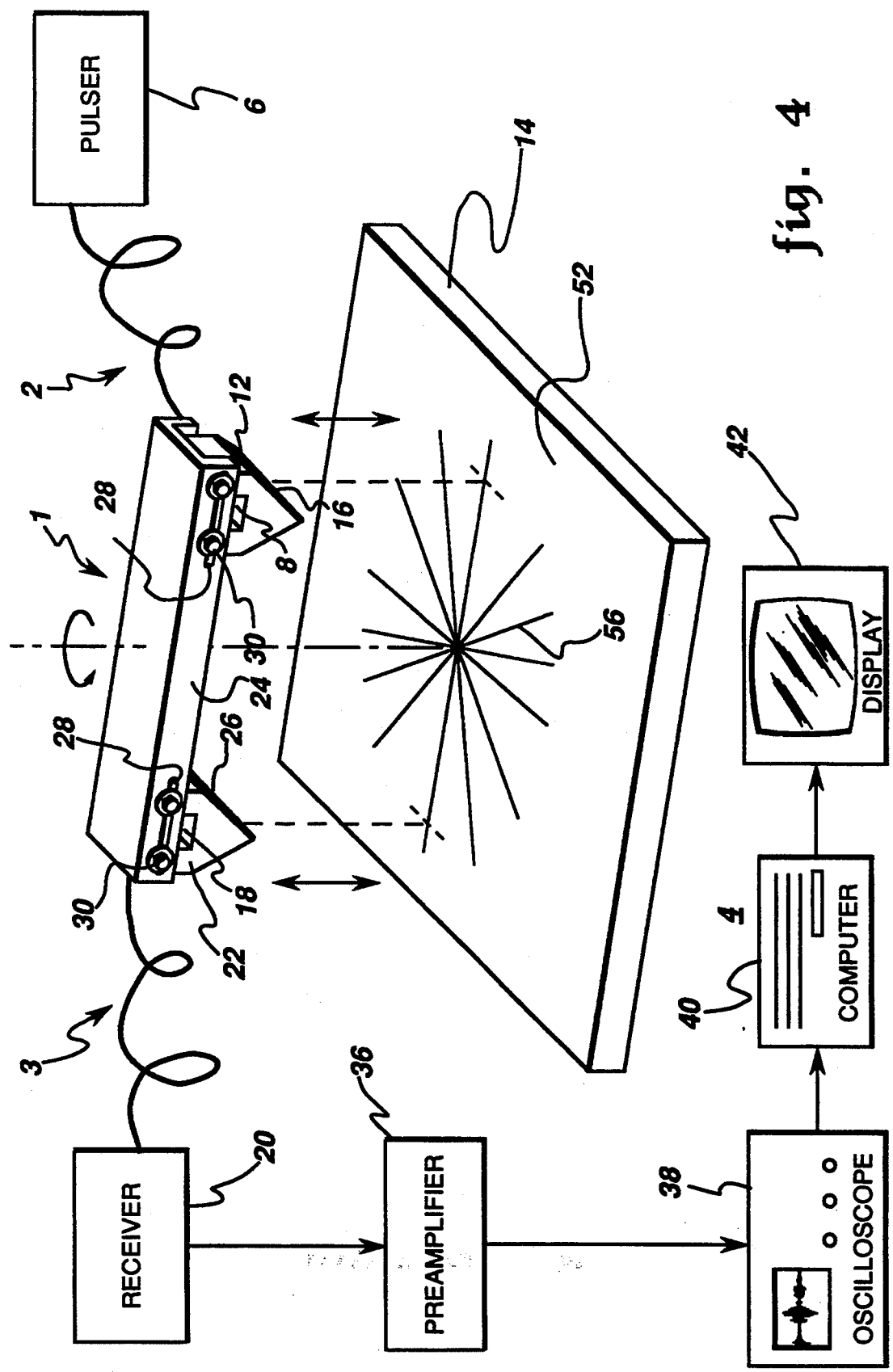
FIG. 4 illustrates a device of one preferred embodiment of the present invention.

Reference is initially made to FIG. 2, which illustrates the various waves generated in a solid by a passage of the ultrasonic wave. Typically in a Lossy medium 44 such as a fiber reinforced composite, the ultrasonic wave is attenuated during the passage through the medium. As depicted in FIG. 2, the first ultrasonic wave to arrive from the point of transmission to the point of detection is usually longitudinal wave 46, the second ultrasonic wave to arrive is usually a transverse wave 48, and the third ultrasonic wave to arrive is usually a Raleigh wave 50, also called a surface wave. The present invention is directed to analyzing first-to-arrive wave 46, also called the first attenuated wave. The electrical signal generated by second transducer 18 (see FIG. 4) may be displayed on oscilloscope 38 (FIG. 4).

Figure 3:
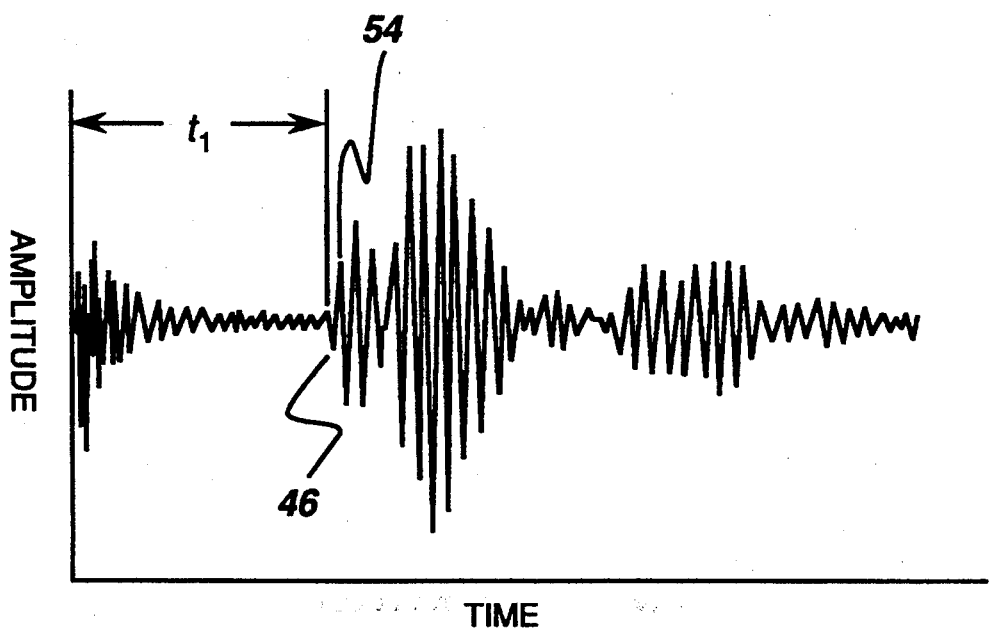
FIG. 3 is a graph of amplitude versus time of the ultrasonic wave during its transmission through the medium.

Details of a displayed signal are further illustrated in FIG. 3. The displayed signal of FIG. 3 provides another representation of longitudinal wave 46 wherein $t_1$ denotes the time interval required for the first attenuated wave to arrive through composite medium 14 from first transducer 8 of focusing means 12 to second transducer 18 of relaying means 22 (FIG. 4).

In general, elastic waves such as the ultrasonic waves propagating through a solid medium will obey a three-dimensional wave equation as noted below;

$$C_{ijkl}s_{m,k}n_j = pv^2 s_i$$

wherein $$i,j,k,l = 1,2,3 \tag{1}$$

where $C_{ijkl}$ are the components of the fourth order stiffness tensor C of the medium, p is the density of the medium, v is the velocity of the ultrasonic wave through the medium, $s_i$ is the wave particle displacement vector, $(n_1, n_2, n_3)$ are direction cosines normal to the wave front, 1,2,3 refer to the orthonormal, Cartesian coordinate axes and a convention of summing over repeat indices is used.

A micromechanical model, initially developed by Christensen, R. and Waals, F., in "Effective Stiffness of Randomly Oriented Fibre Composites", *J. Composite Materials*, 6 (1972), pp. 518–532, and incorporated herein by reference, is extended to predict the stiffness tensor components $C_{ijkl}$ of a fiber reinforced composite having arbitrary two-dimensional, hereinafter 2-D, and three-dimensional, hereinafter 3-D, fiber orientations. By measuring the ultrasonic velocity of the first attenuated wave transmitted through composite medium 14 by measurement device 1, shown in FIG. 4, or by measurement device 200, shown in FIG. 5, and by mathematically fitting the stiffness tensor $C_{ijkl}$ in Equation (1), the density and the fiber orientation of composite medium 14 is determined, as explained below, by solving Equation (1).

The underlying principles in the extended Christensen-Waals micromechanical model used in the present invention are as follows. For any direction in the composite, the numerical value of the ultrasonic velocity is dependent on both the volume fraction of the reinforcement fiber and the average orientation of the fiber direction versus the measurement direction. Key to the ultrasonic characterization of the fiber volume fraction is a theorem that for equivalent fiber and resin compositions and for equal volume fractions, regardless of the lay-up geometry (2-D or 3-D), a three dimensional average of any composite will be the same as a theoretical averaged isotropic composite. This eliminates, from a mathematical standpoint, the effect of fiber orientation. The elastic properties of such composites can thus be uniquely determined by the volume fractions of the phases and the composition of those phases. Therefore by establishing the 3-D distribution, the fiber volume fraction may be determined from either the area of the velocity distribution or the geometric mean velocity.

The fiber volume fraction is defined as percentage by volume of fibers present in the total volume of the fiber reinforced composite medium. If the fiber reinforced composite is substantially void-free, the fiber weight fraction is same as the fiber volume fraction. The model of the present invention also provides the various moduli of elasticity and Poisson's ratio in x, y and z directions. The modulus of elasticity is defined as the stress required to produce unit strain, which may be a change of length (Young's modulus), a twist or shear (modulus of rigidity or modulus or torsion) or a change in volume (bulk modulus). Poisson's ratio is defined as the ratio of transverse contraction per unit dimension of a bar of uniform cross-section to its elongation per unit length, when subjected to tensile stress. In reducing this concept to composite sheets, the concern is now about in-plane (2-D) variations in velocity. For this case, the mean ultrasonic modulus and hence the fiber volume fraction is proportional to the area of the 2-D velocity distribution.

In the Christensen and Waals paper, it is assumed that the stiffness tensor of a completely uniaxially aligned (rotationally isotropic) composite can be calculated from a model such as the composite cylinder model by Hashin, Z. and Rosen, R., *J. Appl. Mech.*, 31,223 (1964), incorporated herein by reference. The properties of a composite with a fiber orientation distribution may be found by averaging the unidirectional properties over the fiber orientation distribution. The aforementioned Christensen and Waals paper dealt with the case of three dimensionally random and two dimensionally random in-plane composites.

The relationships between a stress tensor $\sigma$ and a strain tensor $\epsilon$ are given by the constitutive (cause and effect) equations, shown below. In these equations, where S is the compliance tensor and C is the stiffness tensor, the material properties are contained in the 4th order tensor relating the stress and strain:

$$\sigma_{ij} = C_{ijkl}\epsilon_{kl} \tag{2}$$

$$\epsilon_{ij} = S_{ijkl}\sigma_{kl} \tag{3}$$

$$C = S^{-1} \tag{4}$$

The components of the compliance tensor, S, and the stiffness tensor, C, are usually only known in a frame of symmetry. If the frame of interest is not a symmetric frame, i.e., if the stress or strain state is known in a frame other than the symmetric frame, then either the stiffness tensor C or the compliance tensor S is rotated from the symmetric frame to the frame of interest or the known stress or strain state is rotated to the symmetric frame where the stiffness tensor in Equation (2) or the compliance tensor in Equation (3) are known and the result of the equation rotated back to the frame of interest. In most cases, the choice of whether to use Equation (2) or (3) depends upon the boundary conditions and the ease in solving the equation and transforming the results.

The composite cylinder model of Hashin and Rosen may be used to calculate the five elastic constants needed to describe a rotationally isotropic, unidirectional composite. So long as the microscopic details of the composite are not probed and the actual symmetry of the laminate is not changed through packing considerations, the Hashin-Rosen model can give useful elastic constants.

Bounds on the elastic constants are calculated on an assumption that there is an equivalent amount of energy stored in the composite and a homogeneous material under the same boundary conditions. Four out of the needed five elastic constants can be rigorously calculated from the composite cylinder model of Hashin and Rosen. Using the notation of Christensen and Waals, they are (1-axis=fiber direction):

$$E_{11} = cE_f + (1-c)E_m + \frac{4c(1-c)\mu_m (v_f - v_m)^2}{\frac{(1-c)\mu_m}{k_f + \mu_f/3} + \frac{c\mu_m}{k_m + \mu_m/3} + 1} \quad (5)$$

where $E_{11}$ is the laminate modulus in the fiber direction, $$v_{12} = (1-c)v_m + cv_f + \frac{c(1-c)(v_f - v_m)\left[\frac{\mu_m}{k_m + \mu_m/3} - \frac{\mu_m}{k_f + \mu_f/3}\right]}{\frac{(1-c)\mu_m}{k_f + \mu_f/3} + \frac{c\mu_m}{k_m + \mu_m/3} + 1} \quad (6)$$

where $\mu_{12}$ is the in-plane contraction ratio, $$K_{23} = k_m + \frac{\mu_m}{3} + \frac{c}{\frac{1}{k_f - k_m + (1/3)(\mu_f - \mu_m)} + \frac{1-c}{k_m + (4/3)\mu_m}} \quad (7)$$

where $K_{23}$ is the plane strain bulk modulus, $$\mu_{12} = \frac{\mu_f(1+c) + \mu_m(1-c)}{\mu_f(1-c) + \mu_m(1+c)} \mu_m \quad (8)$$

where $\mu_{12}$ is the shear modulus in the 1-2 plane. It is to be noted that c is the fiber volume concentration, $E_f$ is the Young's modulus for the fiber, $E_m$ is the Young's modulus for the polymer matrix, $v_f$ is Poisson's ratio for the fiber, $v_m$ is Poisson's ratio for the matrix, $k_f$ is the bulk modulus for the fiber, $k_m$ is the bulk modulus for the matrix, $\mu_f$ is the shear modulus for the fiber and $\mu_m$ is the shear modulus for the matrix. Both the matrix and the fiber are assumed here to be isotropic, so $$\mu_i = \frac{E_i}{2(1+v_i)} \quad i = m,f \quad (9)$$

$$k_i = \frac{E_i}{3(1-2v_i)}$$

The fifth parameter may not be determined from the Hashin-Rosen composite cylinder model. There are models for the transverse shear modulus in the literature, but the lower bound from the Hashin-Rosen model is found to be sufficient to provide $$\mu_{23} = \left[1 + \frac{c}{\frac{\mu_m}{\mu_f - \mu_m} + \frac{[k_m + (7/3)\mu_m](1-c)}{2(k_m + (4/3)\mu_m)}}\right] \quad (10)$$

where $\mu_{23}$ is the transverse shear modulus.

These derived values can be related to the five independent components of the stiffness tensor. For the rotationally isotropic case (symmetry axis=1 axis), $$C_{1111} = E_{11} + 4(v_{12})^2 K_{23}$$

$$C_{2222} = C_{3333}\mu_{23} + K_{23}$$

$$C_{1122} = C_{1133} = 2K_{23}v_{12} \quad (11)$$

$$C_{2233} = C_{2222} - C_{2323} = -\mu_{23} + K_{23}$$

$$C_{1212} = C_{1313} = \mu_{12}$$

All others are either zero or equal to the above components.

Since the Christensen-Waals model deals with the effect of fiber distributions by averaging the symmetric state over various angles, the rotational transformation from the symmetric state to the nonsymmetric state is needed. The steps for effecting such a rotational transformation will be readily apparent to one of ordinary skill in this art, and will not be discussed in detail herein. In general, it is preferred to adopt, as a convention on the order of rotations, a standard definition of the Euler angles in effecting transformations from the prime frame to the unprime frame. Spherical coordinate parameters $\theta$ and $\phi$ are appropriately used with reference to the angles of rotation involved in these transformations. A reference source which provides a detailed analysis of the use of rotational transformations in this area is Whitney, J. and McCullough, R., *Micromechanical Materials Modelling*, 2, 1990, Delaware Composites Design Encyclopedia, Lancaster, Pa., pages 3-45 (Introduction to Anisotropic Elasticity), incorporated herein by reference.

As noted previously, the properties of a composite with some type of fiber orientation distribution may be found by averaging the unidirectional properties over the fiber orientation distribution or fiber distribution function $f(\theta,\phi)$. In the case of a 2-D planar distribution, this fiber orientation distribution is preferably represented by an elliptical distribution having no dependence on $\theta$, as follows:

$$f(\theta,\phi) = f(\phi) = \frac{1}{[1 - e^2\cos^2\theta]^{\frac{1}{2}}} \quad 0 \leq e < 1 \quad (12)$$

The Equation (12) elliptical distribution is used in the integration necessary to derive the nine independent stiffness tensor components of, and also ultimately to describe the mechanical properties of, an orthotropic composite.

The parameter e used in defining the fiber orientation distribution $f(\phi)$ represents the eccentricity of the elliptical distribution. When the eccentricity e is 0, the fiber distribution is totally randomized, i.e. there is an equal chance that a fiber will be oriented at any angle $\phi$. Thus, the distribution at e=0 is represented by a circle. However, when the eccentricity e is greater than 0 but less than 1, for example at e=0.5, the distribution will be an ellipse with a major axis coinciding with the fibers having a preferred orientation in the 0° direction (labeled here as the 2 axis), i.e. there is a greater chance that a fiber will be oriented along the 2 axis than the 3 axis.

In both the 2-D and the 3-D analyses, the ultrasonic velocity distribution can be used to determine stiffness tensor C at ultrasonic frequencies, which then can be used to calculate the fiber volume fraction and the fiber orientation. The technique, in summary form, is as follows.

1. It is assumed that the elastic properties of a uniaxial short fiber composite are given by the Hashin-Rosen model, namely the equations therein defining an in-plane contraction ratio and defining a shear modulus in the plane, Equations (6) and (8) herein. From these properties, the components of the stiffness tensor may be derived.

2. The stiffness tensor for orientations other than the symmetric orientation may be obtained by performing a rotational transformation from the symmetric state to the nonsymmetric state.

3. By averaging over the fiber distribution, and by employing a distribution function $f(\theta,\phi)$, the stiffness tensor of the composite may be determined.

4. The stiffness tensor can then be inverted to get the elastic moduli for the composite.

5. The angular distribution of the ultrasonic velocity may be used to determine the fiber orientation and the fiber volume fraction.

Figure 4A:
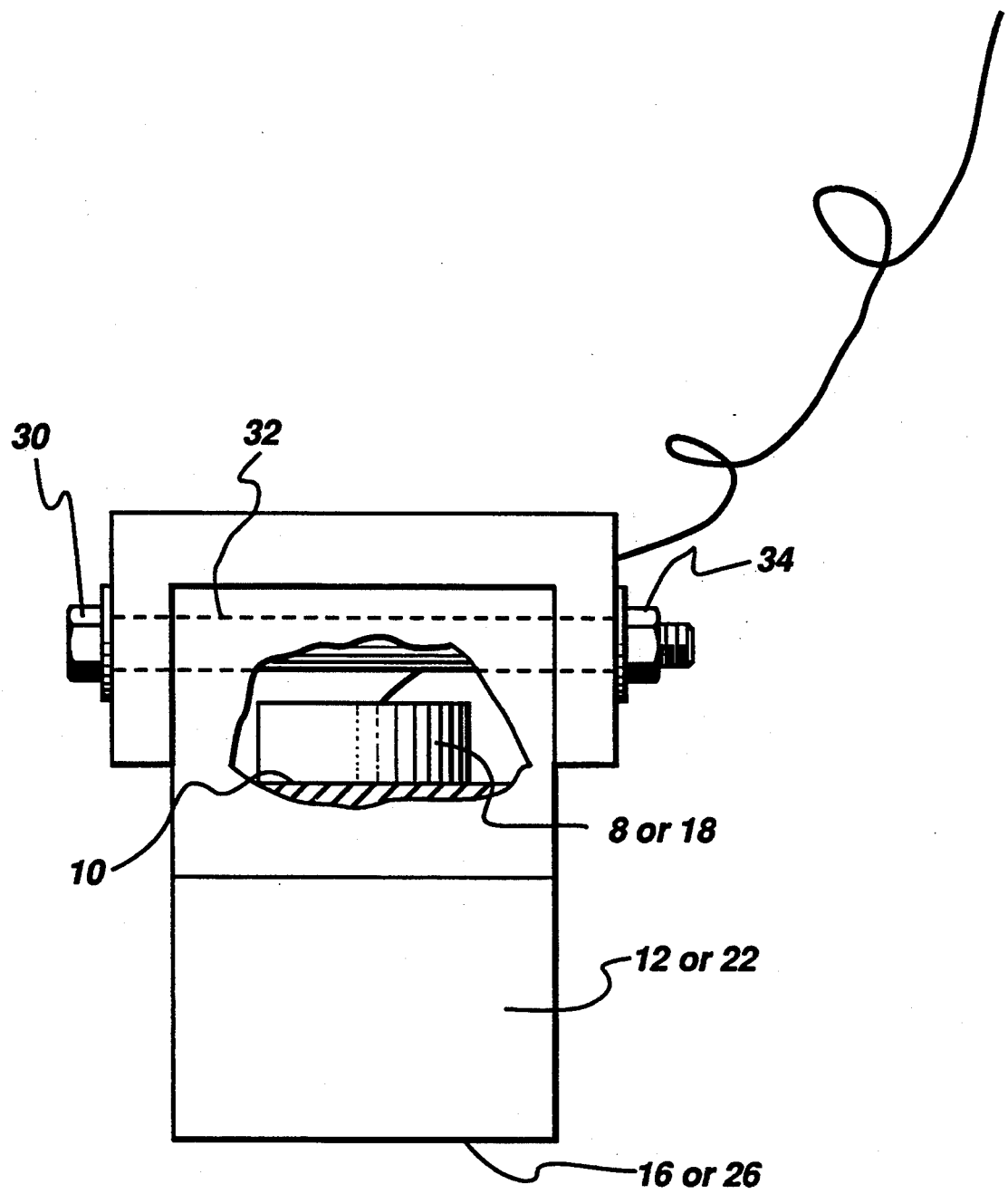
FIG. 4a is a side view of the device of FIG. 4.

Referring now principally to FIG. 4, there is illustrated a basic measurement device, generally designated by numeral 1, for ultrasonically characterizing physical attributes of polymer composites. As shown, device 1 comprises a wave generator means, generally indicated by numeral 2, for generating an ultrasonic wave of a desired frequency. Preferably, wave generating means 2 further comprises an adjustable electrical supply means 6, also called pulser means, for supplying variable power to a first electroacoustic transducer 8 capable of generating an ultrasonic wave of a desired frequency and power. FIG. 4A shows first electroacoustic transducer 8, preferably cylindrical in shape and affixed to a flat surface 10 of focusing means 12. First electroacoustic transducer 8 may be a piezoelectric or a magnetostrictive transducer, however, one made of piezoelectric ceramics containing lead zirconate-titanate (abbreviated as PZT) is preferred. Transducers such as the ones stated below are suitable for use in measurement device 1.

A suitable transducer is about 0.5 inch in diameter, having a miniature size with a standard microdot connector (MSWS style).

Gamma Series Model #PN4539@0.5 MHz;
Gamma Series Model #241-580@1.0 MHz;
Gamma Series Model #242-580@2.25 MHz;
Gamma Series Model #243-580@3.5 MHz;
Gamma Series Model #244-580@5.0 MHz.

All the aforementioned transducers are made by Krautkramer Branson Aerotech Company, Lewistown, Pa. It should be noted that it would be obvious to those skilled in the art to use other styles of transducers for achieving results disclosed in the present invention.

FIG. 4 further shows focusing means 12 used for focusing the ultrasonic wave generated by first transducer 8 into a composite medium 14. It is desirable to substantially match the impedance of focusing means 12 to that of composite medium 14. Preferably, focusing means 12 has a cuneate (wedge) shape with a knife-edged apex 16 in physical contact with composite medium 14, and is made from Plexiglas® polymethyl methacrylate supplied by Rohm & Haas Company, Phila., Pa. when composite medium 14 under analysis is made of glass filled polypropylene. However, to those skilled in the art it will be obvious to change the material of focusing means 14 when some other type of composite medium is analyzed such that the impedances substantially match.

Measurement device 1 further comprises wave converter means, generally indicated by numeral 3, for converting a first attenuated ultrasonic wave after its passage through composite medium 14 into an electrical signal. Wave converter means 3 comprises a second electroacoustic transducer 18, shown in FIG. 4A, and a receiver means 20. Second transducer 18 and first transducer 8 have substantially the same piezoelectric constant and thus form a substantially matched pair. The piezoelectric constant is defined as the ratio of deformation produced on or by the transducer to the voltage applied to or produced by the transducer. It is necessary that first transducer 8 be substantially matched to second transducer 18 so that any qualitative deviation between the ultrasonic wave generated by first transducer 8 and the attenuated ultrasonic wave converted by second transducer 18 into an electrical signal is minimized. Receiver means 20 may be used for receiving the electrical signal generated by second transducer 18 for further analysis. Preferably, electrical supply means 6 and receiver means 20 form a single unit. Preferably, electrical pulses are generated by electrical supply means 6 for exciting first transducer 8, and thus causing it to emit a pulsed ultrasonic wave. The receiving transducer such as second transducer 18 receives and converts the pulsed ultrasonic wave, which is attenuated during transmission through medium 14, into an electrical signal which is then received and conditioned by receiver 20 for further analysis. A suitable pulser/receiver, such as Model #5055PR made by Panametrics, Waltham, Mass., may be used.

Second transducer 18 may be affixed to a relaying means 22, having substantially identical shape and made from substantially identical material as focusing means 12. Therefore, it is understood that the subassembly of first transducer 8 and focusing means 12 is substantially matched in shapes and materials of fabrication to that of second transducer 18 and relaying means 22. Thus, FIG. 4A may be also referred to for observing the placement of second transducer 18 on relaying means 22.

Preferably, as shown in FIG. 4, focusing means 12 and relaying means 22 are secured to a supporting member 24 having a lower propagation velocity than that of composite medium 14. This will be true, for example, if supporting member 24 has a higher impedance than that of composite medium 14. The ultrasonic wave generated by first transducer 8 will pass through composite medium 14 and also through support member 24. However, by providing support member 24 with higher impedance than composite medium 14, the ultrasonic wave will pass through composite medium 14 first, before it passes through support member 24, thereby ensuring that the first attenuated wave received by second transducer 18 is received through composite medium 14 and not through support member 24. Preferably support member 24 is made of DELRIN® acetal polyamide, supplied by DuPont de Nemours, Inc., Wilmington, Del., when measurement device 1 is used for characterizing physical attributes of the glass filled polypropylene composite medium. However, to those skilled in the art it will be obvious to utilize other materials suitably matched for other types of composite media.

The distance between apex 16 of focusing means 12 and apex 26 of relaying means 22 may be varied by a slidable adjustment provided by a sliding means disposed on support member 24, preferably through an opposing pair of slots 28, located on support member 24. Focusing means 12 and relaying means 22 each may be supported by means of a pair of anchoring bolts 30 which pass through slots 28 located on support member 24 and shown in FIG. 4, and through holes 32 located on focusing means 12 and relaying means 22 and shown in FIG. 4A, wherein anchoring bolts 30 are secured by nuts 34. However, to those skilled in the art other types of securing means would be apparent.

Measurement device 1 preferably further comprises preamplifier means 36 used for performing a high gain/low noise amplification of extremely weak electrical signals generated by second transducer 18, before the signal is fed into additional amplifier circuits. Preamplifier 36 is typically suitable for a specific frequency range of the ultrasonic wave. Measurement device 1 preferably provides three different preamplifiers, however it will be apparent to those skilled in the art to add additional preamplifiers for covering a wider frequency range of the ultrasonic wave generated in measurement device 1. Suitable preamplifiers produced by Panametrics Corp., Waltham, Mass., and having the model numbers 5660B for 0.02–2.0 MHz bandwidth, 5662 for 0.5–5.0 MHz bandwidth and 5670 for 0.5–10.0 MHz bandwidth may be used.

Measurement device 1 is further provided with a processing means, generally indicated by numeral 4, for transferring the electrical signal generated by second transducer 18. Preferably, processing means 4 comprises an analyzing device such as an oscilloscope 38 for providing a visual display of the signal, a computer 40 for determining the physical attributes of composite medium 14 and a display device 42 such as a CRT screen for displaying the physical attributes processed by the computer 42, which may be of any conventional design such as a Personal Computer AT, Model No. 5170, made by IBM Inc., Armonk, N.Y. A conventional printer may be substituted for or added to display device 42. Oscilloscope 38 may be of any conventional design, such as a Model #2430 made by Tektronix, Beaverton, Oreg. Display device 42 may be also of any conventional design, such as a Model No. 5154001 (Enhanced Color Display) made by IBM Inc., Armonk, N.Y. However, it will be apparent to those skilled in the art to use other suitable equipment as the processing means of the preferred embodiment.

Figure 5:
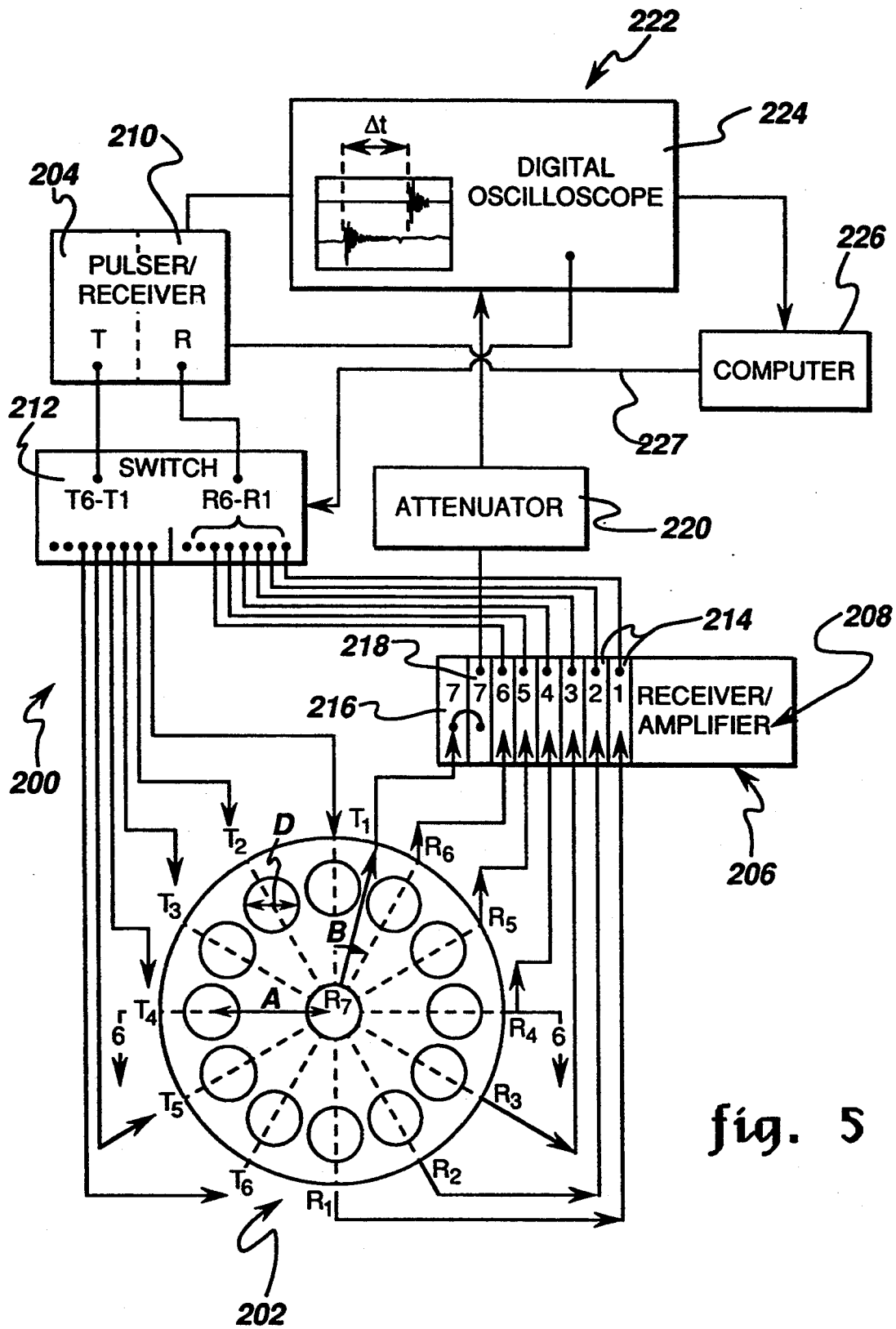
FIG. 5 illustrates a device in accordance with another preferred embodiment of the present invention, in substantially schematic form.
Figure 6:
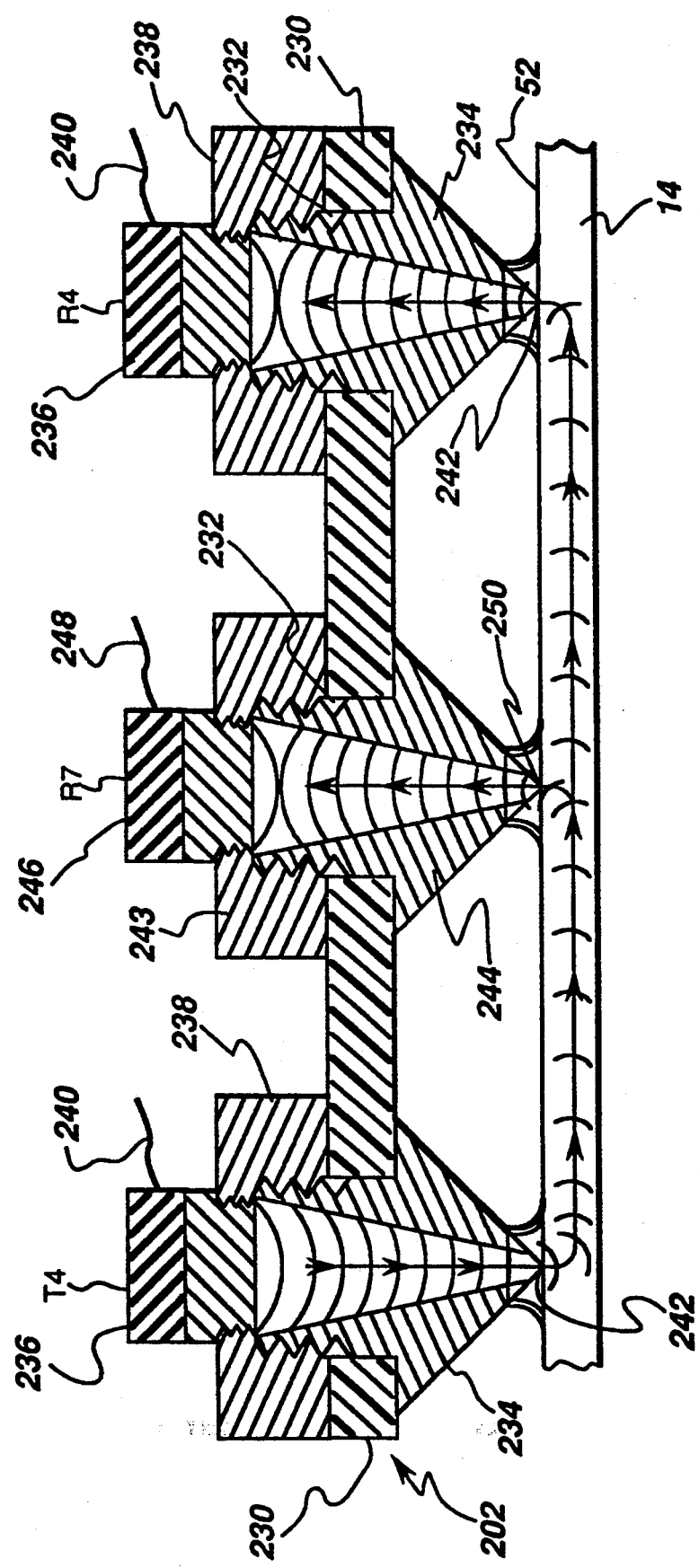
FIG. 6 is a cross-section view of the transducer mounting assembly of the device of FIG. 5, taken at section line 6—6, in partially schematic form.

Another preferred embodiment of the present invention is illustrated in FIG. 5, with a cross-section of the transducer mounting assembly employed in the FIG. 5 device being shown in FIG. 6. In this preferred embodiment, the measurement device 200 employs a transducer mounting assembly 202 which is designed to carry a plurality of diametrically opposed pairs of ultrasonic transmitting (circles T1–T6) and receiving (circles R1–R6) transducer assemblies circularly arranged thereon. In addition, a receiving transducer assembly R7 is to be provided at the center of the circular arrangement. The constructional details of the transmitting and receiving transducer assemblies will be discussed in further detail in a later portion of the specification directed to FIG. 6.

As was the case with the FIG. 4 and 4a embodiment, other major components of the device 200 include an ultrasonic wave generating means 204, referred to also as an electrical supply means or pulser means, and a wave converter means 206, which includes receiver/amplifier means 208 and receiver means 210, which is preferably integral with pulser means 204. Because this embodiment employs a plurality of transmitter/receiver pairs, a multiple channel digital switch means 212 is provided at the output of pulser means 204 and at the input of receiver means 210. The digital switch preferably has at least as many channels as there are pairs of transmitting and receiving transducers, with six pairs being shown in FIG. 5.

Receiver/amplifier means 208 is interposed between the receiving transducer assemblies R1–R6 and the digital switch means 212. In the depicted preferred embodiment, the receiver/amplifier means comprises a plurality of in-line receiver/amplifiers, with one receiver/amplifier 214 provided for each of receiving transducer assemblies R1–R6, and with two receiver/amplifiers 216, 218 provided for the central receiving transducer assembly R7. Each receiver/amplifier preferably provides 40–60 dB amplification of the signals received by the receiving transducers. The receiver/amplifiers associated with and connected to the receiver transducers R1–R6 are connected at their outputs to corresponding channels of digital switch means 212.

The output from the second 218 of the two receiver/amplifiers connected to central receiving transducer R7 is connected to an attenuator 220 which may be used to control the sensitivity of receiving transducer R7. The attenuator is preferably capable of providing from 0–60 dB attenuation, with the level to be changeably set by switching.

The output signals of receiver means 210 and attenuator 220 are preferably sent to a processing and display means 222, which, in the depicted embodiment, comprises a two-channel digital oscilloscope 224 and a computer 226, both of which can be selected from among a number of commercially available products. The computer 226 is provided to receive an output from the digital oscilloscope in the form of digitized waveforms, for further processing in conducting the method of the present invention. The computer 226 is also coupled to digital switch means 212, in a manner such that the computer can send a digital signal to the switch means 212 to effect a switching to successive channels over which subsequent ultrasonic velocity readings will be made.

It is contemplated that a "manual" form of the FIG. 5 device can be provided, in which either no computer 226 is provided, or the computer is not employed to effect channel switching and/or processing of received signals to determine velocities of ultrasonic waves through the material under investigation. In the "manual" variation of this embodiment, the digital switch 212 may be made manually switchable, and the necessary readings for calculation of ultrasonic velocity may be taken from the digital oscilloscope, as will be discussed further with respect to the steps involved in carrying out the method of the invention.

FIG. 6 illustrates, in substantially schematic form, a cross-section view of the transducer mounting assembly 202 taken at section line 6—6 of FIG. 5. Mounting disc 230, which preferably has a thickness on the order of ⅛ inch, is made of a low velocity polymer for the same reason that a low velocity polymer was selected for track 24 in the FIG. 4 embodiment, namely to ensure that a first-received ultrasonic pulse is one which has traveled through the part being examined, and not through the disc 230 itself. Mounting disc 230 has throughholes 232 at a center thereof and at a plurality of locations spaced equidistantly from the center. In one preferred embodiment, each throughhole will be 0.75 inch in diameter D (FIG. 5), and the center-to-center distance A (FIG. 5) between the central throughhole and each surrounding throughhole is 2.0 inches.

As can be seen also by referring back to FIG. 5, in the depicted preferred embodiment there are six pairs of diametrically opposed throughholes, spaced apart at 30° intervals B near a periphery of disc 230. It will be readily understood that fewer than six pairs or greater than six pairs may be suitable for any particular use, and that it is preferred to have the pairs spaced at equal angles around the center.

Each of the transmitter and receiver/transducer assemblies T1-T6, R1-R6, preferably has the same basic construction. Each assembly comprises a focusing wedge means 234 and a transducer 236. In the depicted preferred embodiment, an upper portion of focusing wedge means 234 is threaded, a lower portion of transducer 236 is threaded, and an aluminum holding nut 238 having internal threads corresponding to the threaded portions of the focusing wedge means and transducer is provided to secure the assembly T4,R4 to the mounting disc 230. Holding nut 238 is designed to be positioned atop mounting disc 230, and when the threaded upper portion of focusing wedge means 234 is threaded into holding nut 238 from the lower side of mounting disc 230 through throughhole 232, these members operate to clamp the assembly to the disc 230. The transducer 236 may then be threaded into its position atop focusing wedge means 234. The transducer 236 from assembly T4 is preferably connected to the pulser means 204, and the transducer 236 of assembly R4 is preferably connected to receiver/amplifier means 208, by microdot connectors 240, which are well known in the art for use with ultrasonic transducer assemblies.

The focusing wedge means 234 of each assembly T1-T6 and R1-R6 is preferably of a wedge shape like that of focusing means 12 and the relaying means 22 of the FIG. 4, 4a embodiment, in which the wedge tapers to substantially a linear knife-edge contact surface 242, with the included angle being 60°. Focusing wedge means 234 is preferably made of the same material as that described for use in the FIG. 4 embodiment.

The transducer elements 236 may be either circular or square, and may emit either focused or unfocused ultrasonic beams. The transducer frequency used may preferably be in a range of 0.5–5.0 MHz, and may be selected to provide optimal performance based upon the expected elastic properties and attenuation of the material to be subjected to examination. Such optimization would be particularly advantageous in cases where successive pieces of a similar material are to be examined as part of a manufacturing quality control program.

The focusing wedge means 234 operates to cylindrically focus the ultrasonic beam emanating from the transmitting transducer 236 to concentrate the beam at the wedge tip. It is also preferred, in order to maximize the concentration of the beam, to employ cylindrically focused transducer elements for transducer elements 236, which are generally known in the art.

Central receiving transducer assembly R7 is preferably secured to mounting disc 202 in the same manner as transducer assemblies T1–T6, R1–R6. An aluminum holding nut 243 threadingly engages external threads disposed on central focusing means 244 and on central receiving transducer 246. Central receiving transducer 246 is operatively connected to receiver/amplifier means 216 by a microdot connector 248

Central focusing means 244 may preferably be made of the same material as focusing wedge means 234; however, the central focusing means is preferably of a different geometry or shape. The central transducer is disposed to receive signals from each of transmitting transducer assemblies T1–T6 as the signal or wave propagates across to the associated receiving transducer assembly R1–R6. As such, it is preferred that the central focusing means tapers in a conical shape to present to the material being examined substantially a point contact 250, as compared with the knife-edge contact of the focusing wedge means 234 employed with assemblies T1–T6, R1–R6. It is also preferred that central receiving transducer element 246 be spherically focused to a point at the tip 250 of central focusing means 244, which is preferably positioned at a common beam-crossing point in the center of the material being evaluated, to ensure that consistent signals will be received from each of the transmitting transducers.

Figure 7A:
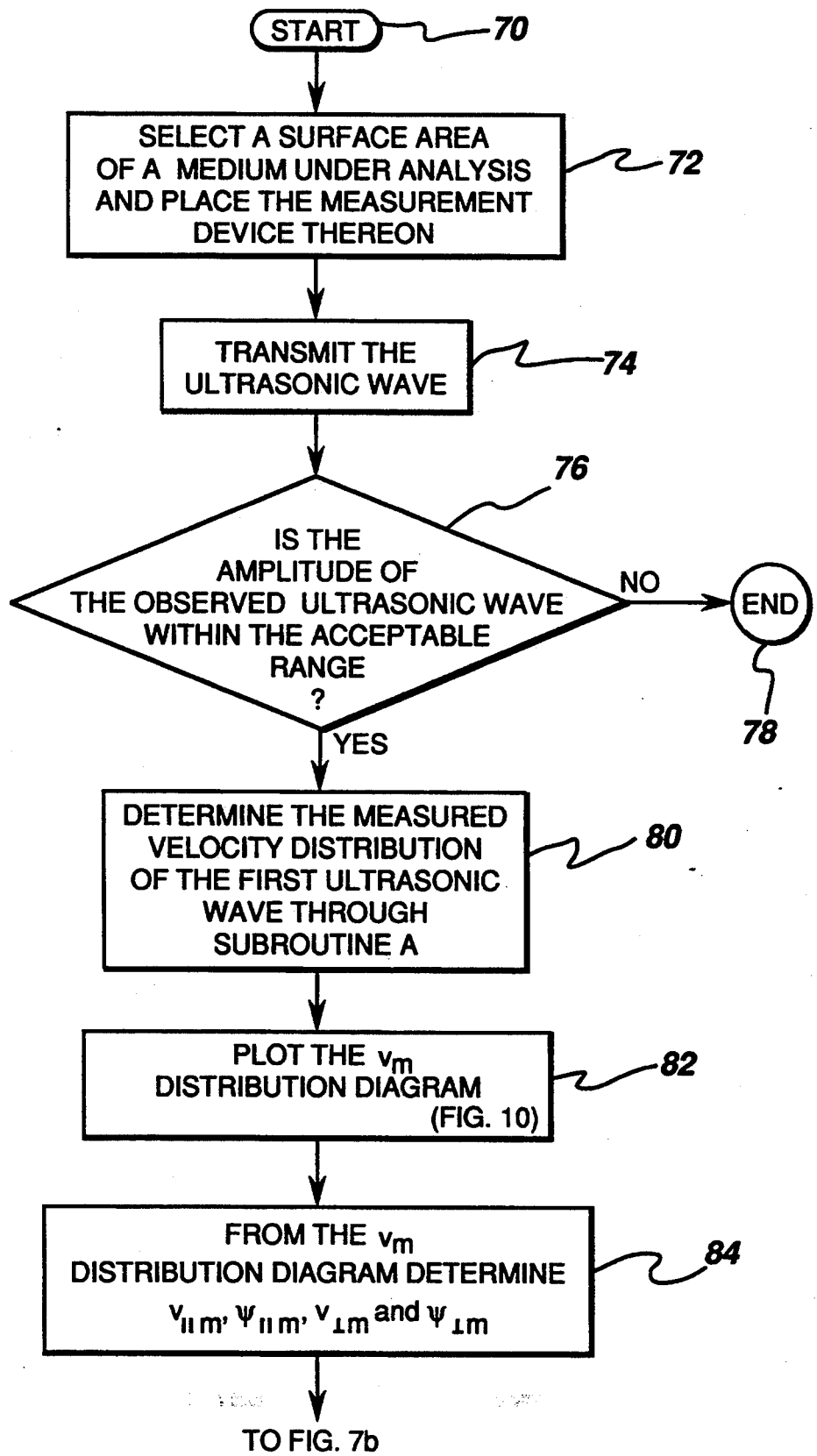
FIGS. 7a, 7b and 7c are flowcharts illustrating an operation of the preferred embodiment shown in FIG. 2.
Figure 7B:
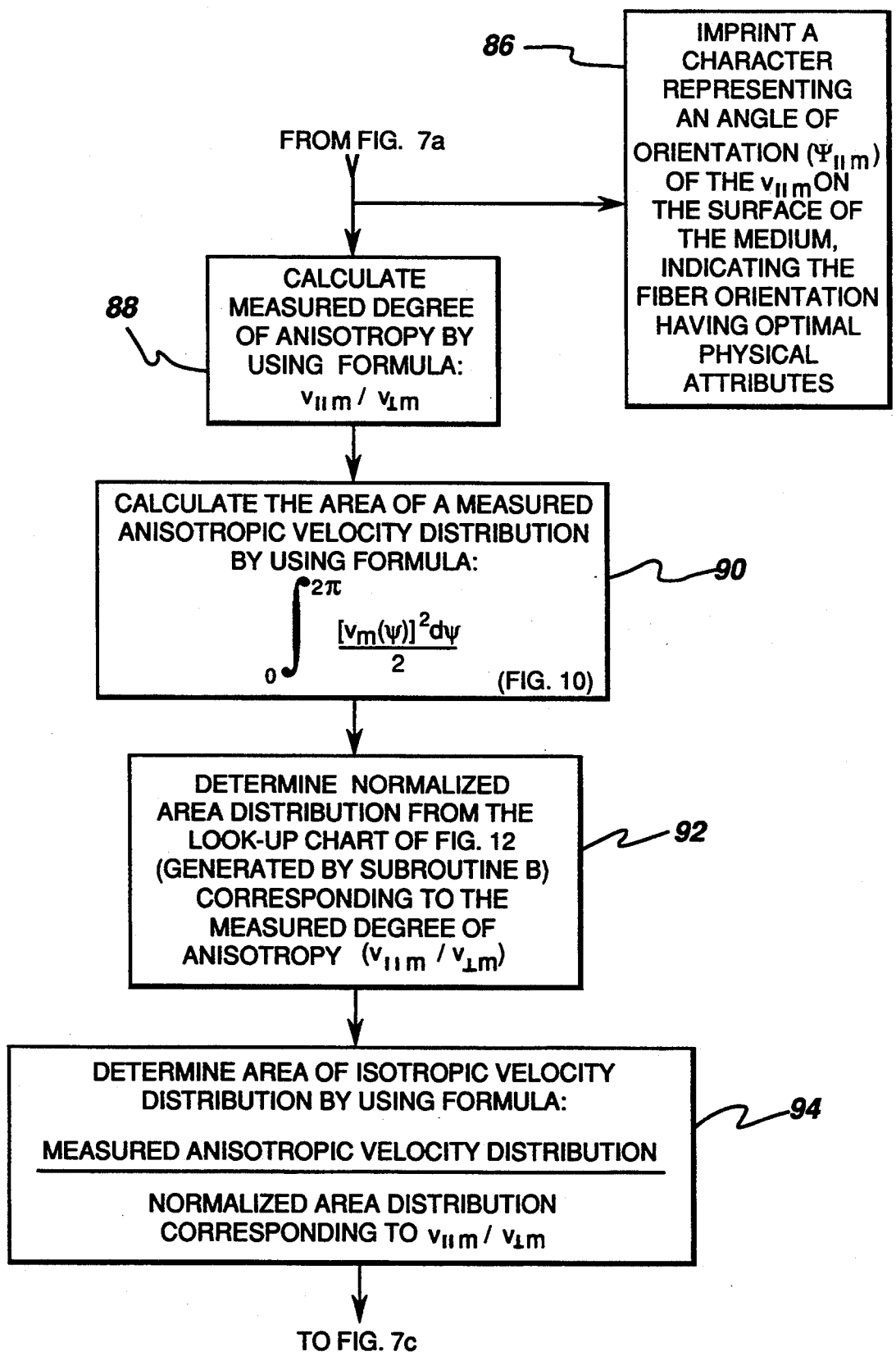
Figure 7C:
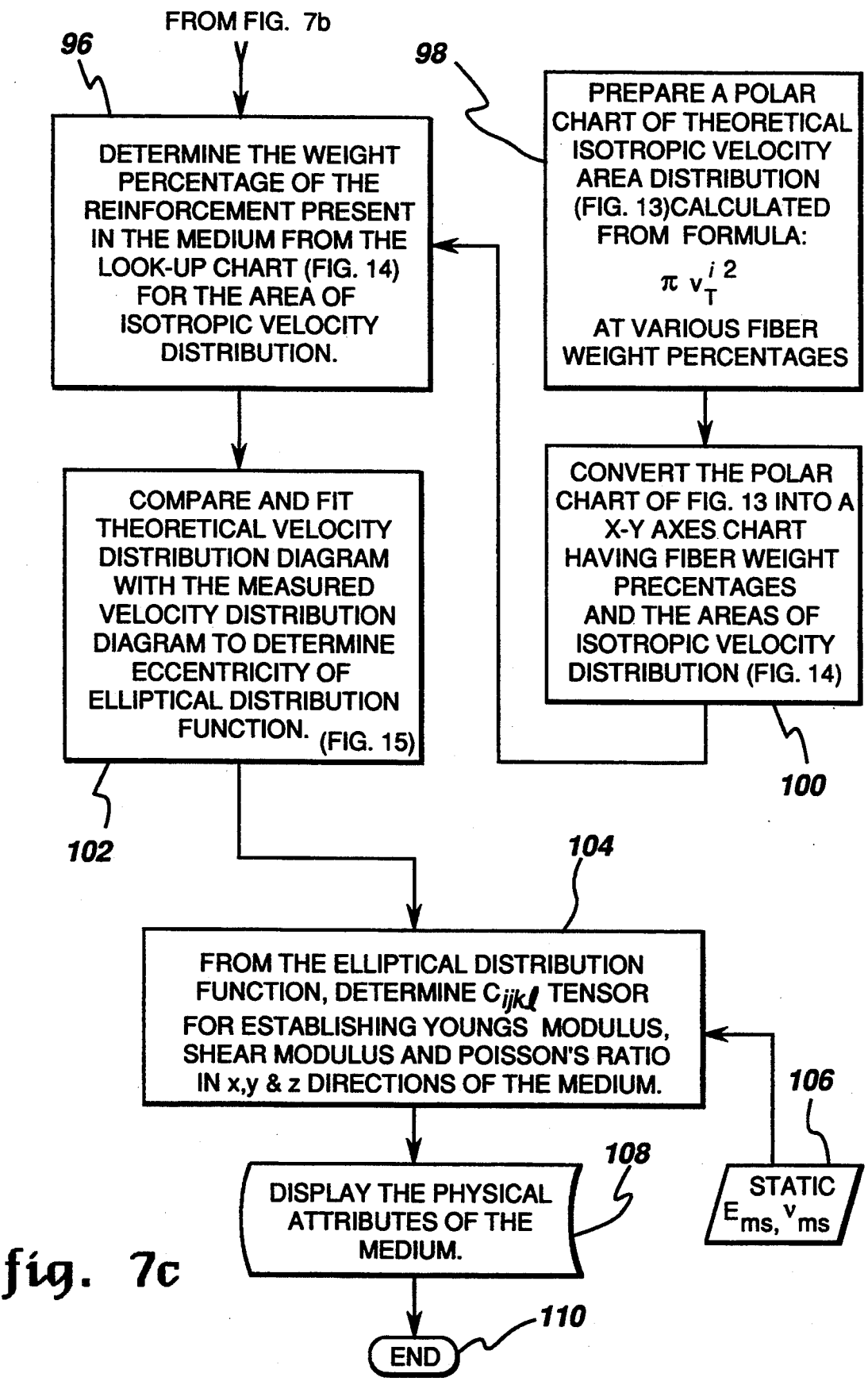
Figure 8:
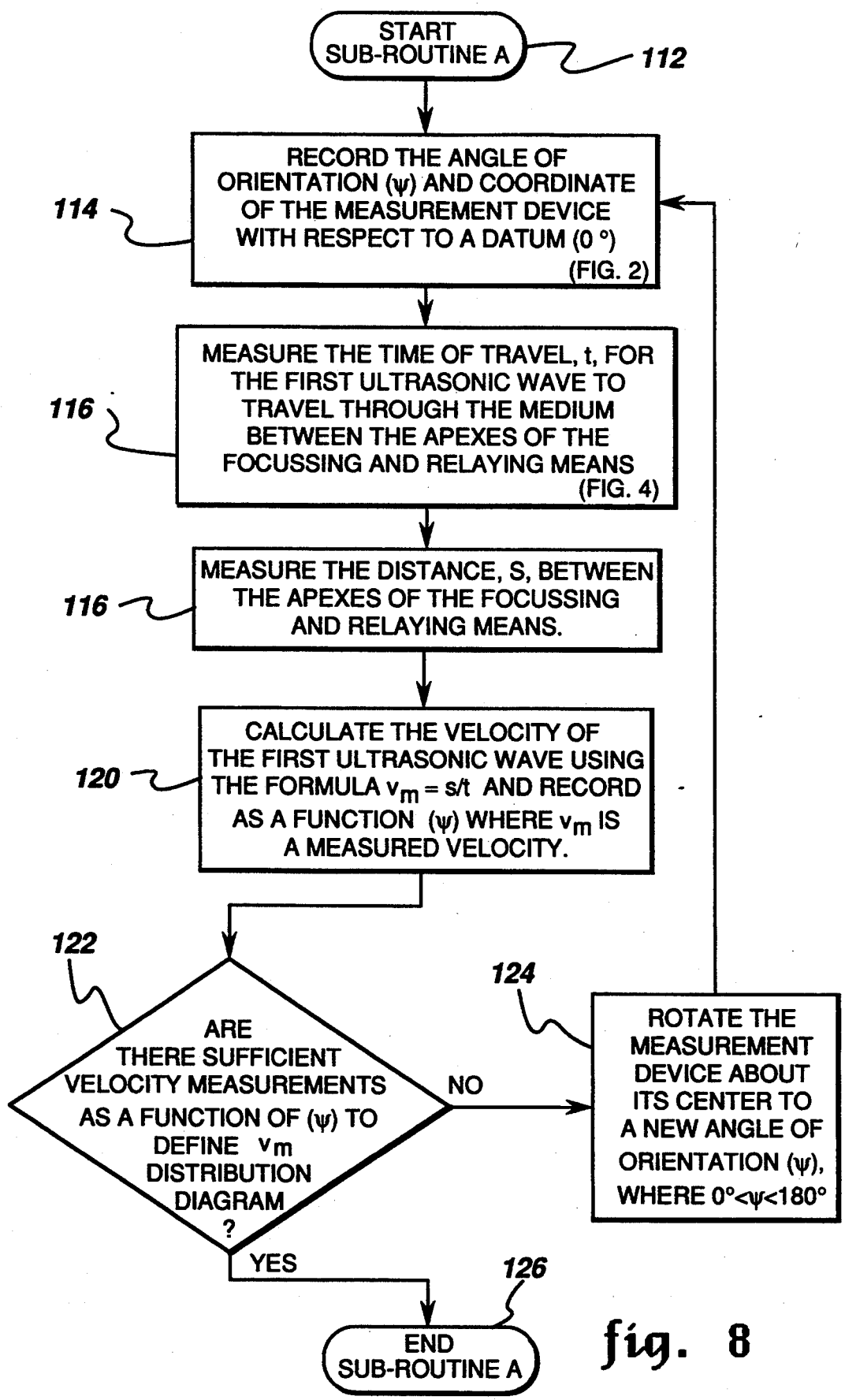
FIG. 8 is a flowchart of a subroutine A further illustrating the operation of the preferred embodiment shown in FIGS. 7a, 7b and 7c.
Figure 9:
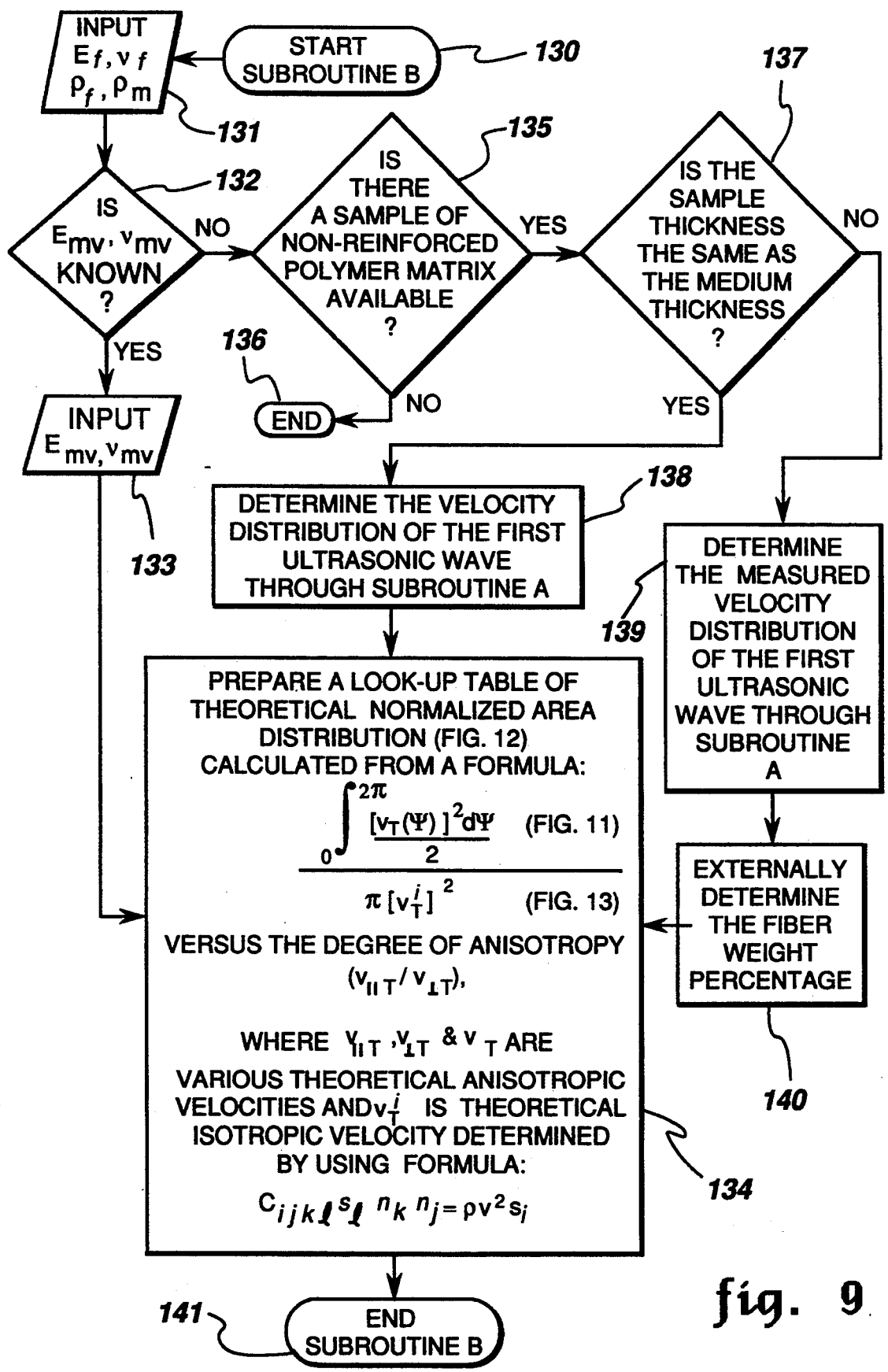
FIG. 9 is a flowchart of a subroutine B further illustrating the operation of the preferred embodiment shown in FIGS. 7a, 7b and 7c.

Turning now to a detailed description of a procedure used by processing means 4 of the FIG. 4 embodiment or, with minor variations which will be discussed later, by the processing means 222 of the FIG. 5 embodiment, the flowcharts of FIG. 7a through 7c show the various steps executed in carrying out the procedure. Additionally, the flowcharts of FIG. 8 and FIG. 9 illustrate subroutines A and B, respectively. The subroutines A and B provide the additional steps required for carrying out the procedure. The procedure illustrated in FIGS. 7a, 7b, 7c, 8 and 9 set forth the program steps generally followed by computer 40 of FIG. 4 in determining the physical attributes of fiber reinforced composite medium 14. The processing program steps are adapted to the particular features of pulser 6, receiver 26, preamplifier 36, oscilloscope 38, computer 40, first transducer 8 and second transducer 18

At start 70 of the program in FIG. 7a, an area of substrate to be analyzed is selected in step 72. The present invention may be utilized for a substrate comprising a medium or a matrix of a thermoplastic or a thermoset polymer reinforced with fibers, flakes, beads or particles comprising materials such as glass, carbon, steel, polyamide or talc powder. Thermoplastic polymer materials such as polyethylene, polypropylene, polystyrene, polyetherimide, polycarbonate, or polyester may be used.

In step 74, device 1 shown in FIG. 4 is then placed on a selected surface 52 of medium 14 and an ultrasonic wave of known frequency and amplitude is transmitted through medium 14. It should be understood that, in order to determine the physical attributes of medium 14 being examined, medium 14 should be substantially free from voids sometimes formed by the air pockets trapped within medium 14 during its manufacture. However, a medium that is up to about 95% void free can be successfully analyzed by device 1

In step 76, the composite medium 14 under analysis is checked to ensure that it is substantially void-free by comparing the amplitude 54 shown in FIG. 3 of the ultrasonic wave with the amplitude of a known, substantially void-free substrate medium also called a control medium, having substantially the same thickness as composite medium 14 under analysis. The amplitude of composite medium 14 is then compared with the amplitude of the control medium. If the amplitude of the test medium is same as or up to 95% of the amplitude of the control medium, the steps of the process are continued further.

Figure 10:
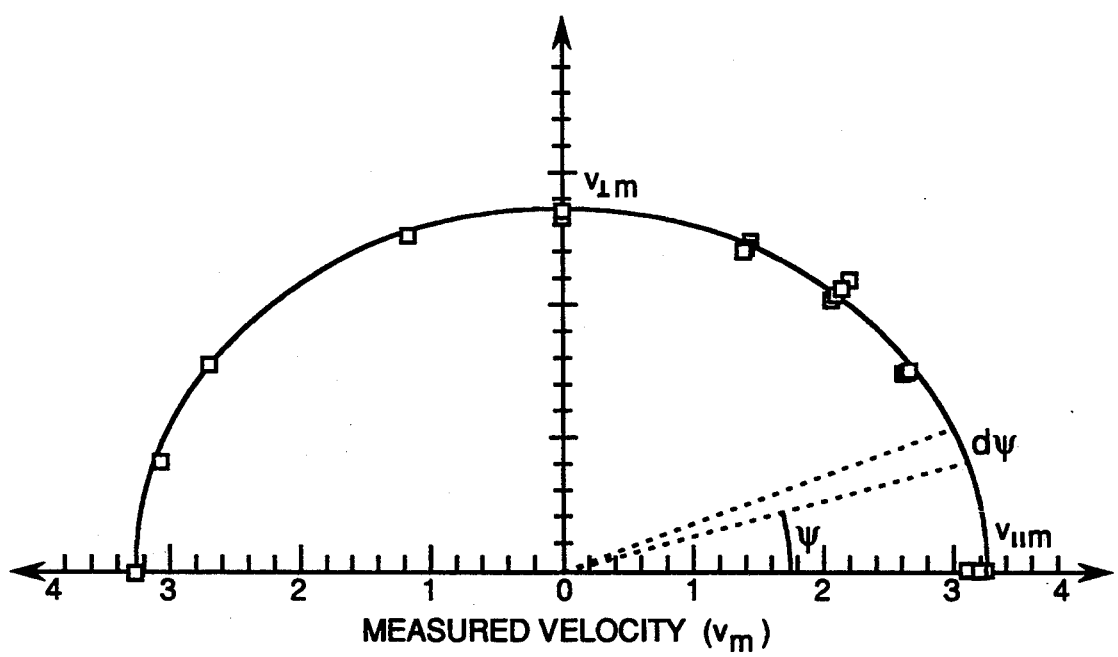
FIG. 10 is a polar graph of a measured velocity ($v_m$) of the ultrasonic wave through the medium and an angle of orientation ($\Psi$) of the device shown in FIG. 2 with respect to a datum.

By using the steps of subroutine A, shown in FIG. 8, a sufficient number of measured velocities($v_m$) are obtained and a measured velocity distribution diagram as shown in FIG. 10 is plotted. From the diagram of FIG. 10, $v_{maximum}$ (also referred to as $v_{l/m}$), $v_{minimum}$ (also $v_{\perp m}$), the angle of orientation of $v_{maximum}$ ($\Psi_{llm}$) and the angle of orientation of $v_{minimum}$ ($\Psi_{\perp m}$) are extracted. If required, as shown in step 86 of FIG. 7b, characters representing $\Psi_{llm}$ and $\Psi_{\perp m}$ may be imprinted on surface 52 of medium 14 to indicate the fiber orientation within medium 14 having optimal physical attributes. Generally the physical attributes such as Young's modulus are optimal in a direction parallel to the angle of fiber orientation $\Psi_{llm}$ and $\Psi_{\perp m}$. To those skilled in the art, it will be obvious to provide means such as closed loop robotic device having means to convert a computer digital output into an analog signal capable of guiding an arm of a robot to imprint a character such as an arrow on surface 52.

The next step 88 performed by processing means 4, shown in FIG. 7b, comprises calculating the measured degree of anisotropy using the formula $v_{llm}/v_{\perp m}$. This measured degree of anisotropy relates to the anisotropic behavior exhibited by fiber reinforced medium 14, which results from the presence of fibers having some degree of orientation.

The area of the measured anisotropic velocity distribution as shown in FIG. 10 is then calculated by using the formula shown in a step 90 of FIG. 7b.

Figure 12:
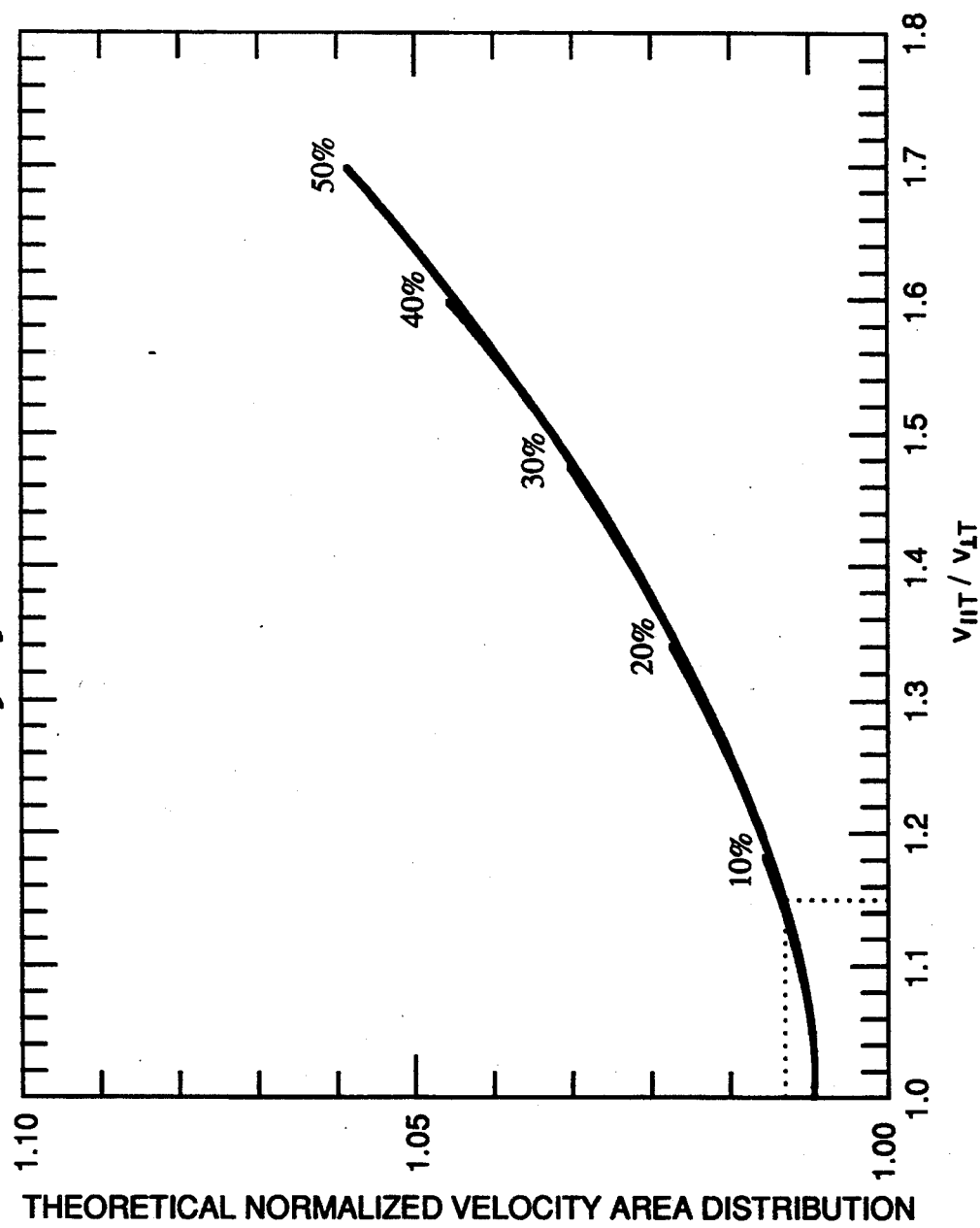
FIG. 12 is a graph of theoretical normalized velocity area distribution versus ratio of maximum theoretical velocity ($v_l/T$) to minimum theoretical velocity ($v_\perp T$) at various fiber percentages present in the fiber reinforced composite medium.
Figure 13:
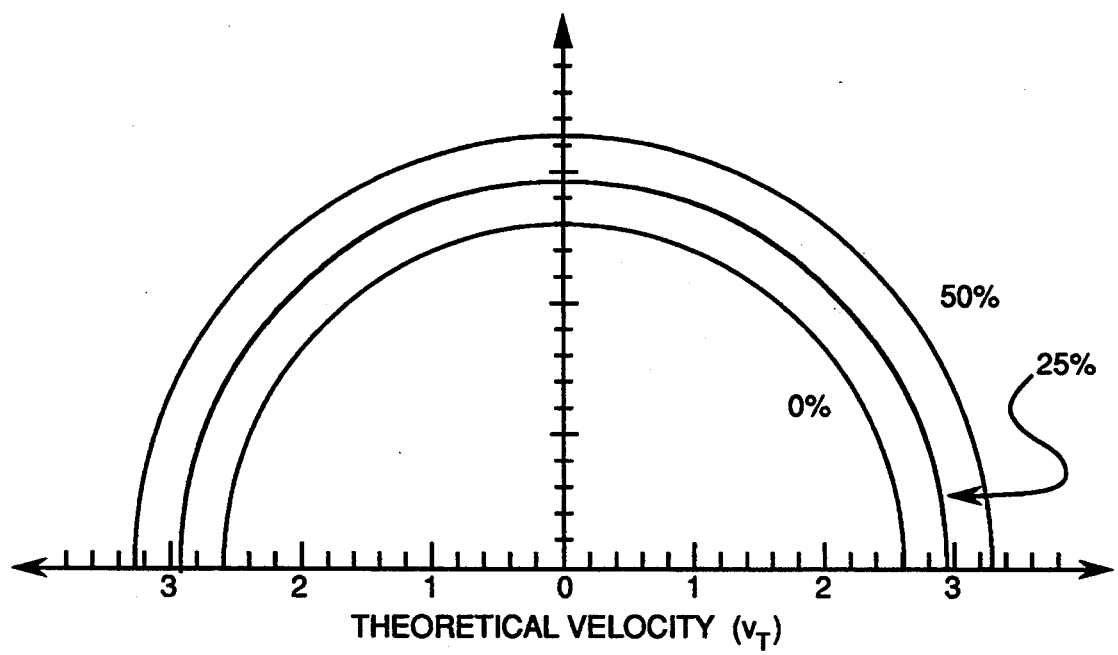
FIG. 13 is a polar graph of theoretical isotropic velocity area distribution versus the fiber weight percentage in the medium.

The normalized area distribution for $v_{llm}/v_{\perp m}$ is determined in step 92 from a lookup chart of FIG. 12, generated through the steps disclosed in subroutine B of FIG. 9. In step 94, an area of isotropic velocity distribution is determined from the ratio of measured anisotropic velocity distribution to normalized area distribution corresponding to $v_{llm}/v_{\perp m}$ of step 92. In step 96, shown in FIG. 7c, the weight percentage of the reinforcement present in medium 14 corresponding to the area of isotropic velocity distribution of step 94 is determined, through the chart of FIG. 14. The chart of FIG. 14 was prepared in step 98, by first preparing a polar chart of the theoretical isotropic velocity areas at various fiber weight percentages and then, as shown in step 100, converting the polar chart of FIG. 13 into the x-y axes chart of FIG. 14.

Figure 14:
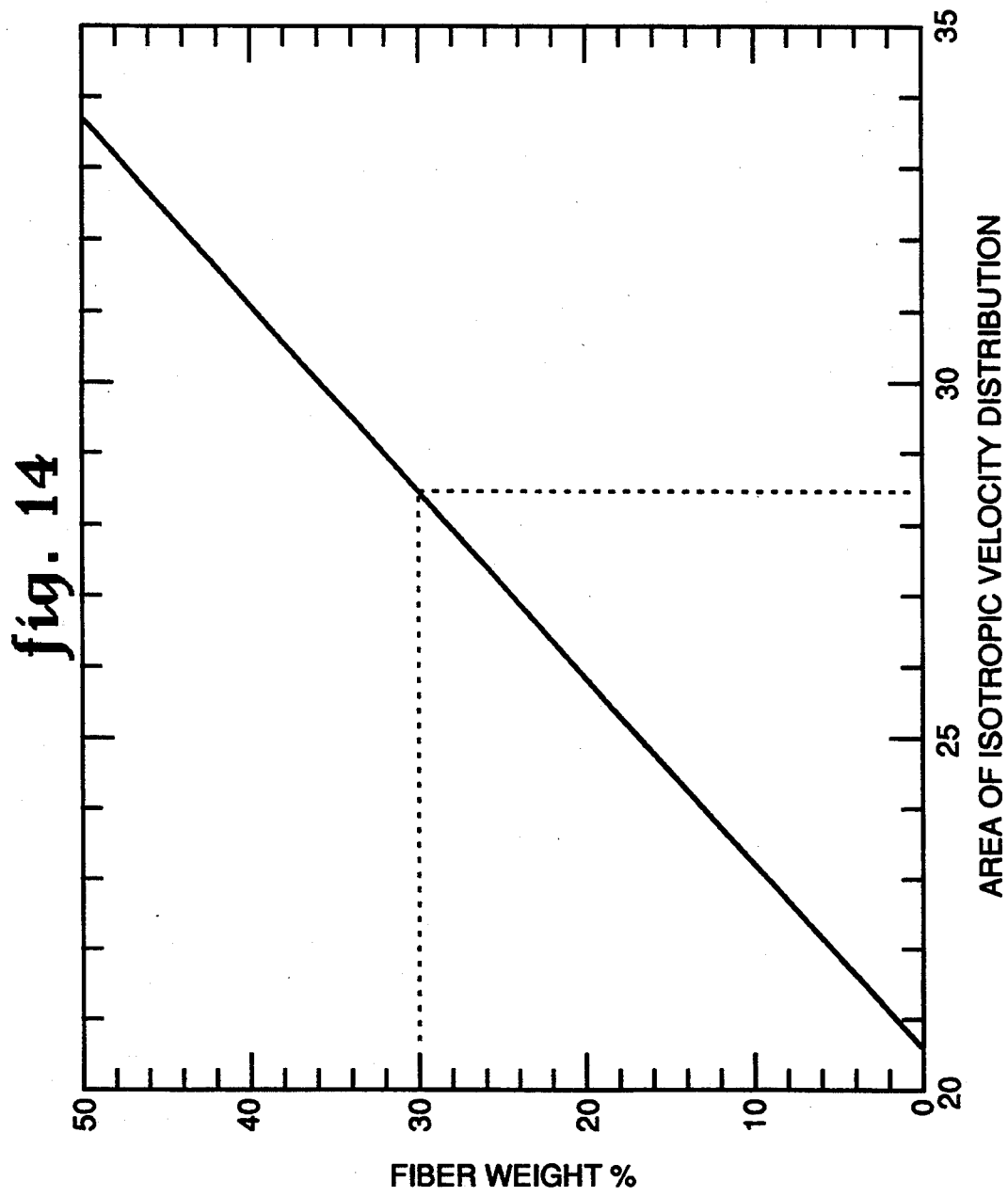
FIG. 14 is a graph of the area of isotropic velocity distribution versus the fiber weight percentage in the medium.

The data in FIG. 14 is, in essence, values of volume fraction of fiber reinforcement (fiber weight percentages) represented as a function of the theoretical area of isotropic velocity distribution. This data may be stored in the form of a lookup table in processing means 4, or can be defined in an operating program by the functional relationship. The former would permit a determination of volume fraction of reinforcement by looking up the measured area of isotropic velocity distribution as determined in step 94 and obtaining the value for volume fraction at that point. The latter approach would involve the program performing mathematical operations to solve the functional relationship, using the "area" variable, to find the "volume fraction" variable.

In step 102, the last factor necessary to solve Equation (1) is determined. Essentially step 102 comprises generating various velocity diagrams, shown in FIG. 15, at various eccentricities (e), and matching and fitting one of them with the measured velocity distribution diagram, which thereby determines the eccentricity (e) of the elliptical distribution function.

As shown in step 104 of FIG. 7c, once the eccentricity (e) is determined, it is plugged into Equation (1) along with inputs 106 of static Young's modulus ($E_{ms}$) and Poisson's ratio ($v_{ms}$) of the matrix material to determine the $C_{ijkl}$ tensor, and thereby determining the physical attributes, such as Young's modulus, shear modulus and Poisson's ratio, in x, y, and z directions of the fiber reinforced composite medium 14.

The attributes are then displayed, in step 108, on CRT screen 42 and/or printed by a printer 43 controlled by computer 40.

Subroutine A of FIG. 8 provides the steps 112 through 126 necessary, when employing the FIG. 4 embodiment of the measuring device, for determining the velocities of the ultrasonic wave passing through the medium at several angles of orientation ($\Psi$) of device 1. The FIG. 5, 6 embodiment simplifies the taking of the measurements, as will be discussed later.

Referring to FIG. 4 and FIG. 8, surface 52 of medium 14 being analyzed is identified or otherwise imprinted with markings 56, aligned to various angles of orientation ($\Psi$). It will be apparent to those skilled in the art that markings 56 on medium 14 may be replaced by having device 1 attached to either a robot or a turntable having predetermined positions corresponding to angles of orientation ($\Psi$) at which device 1 may be positioned in accordance with a predetermined program. Also, in the alternative preferred configuration of FIGS. 5, 6, it will readily be seen that the need for markings or any means for automatically rotating the focusing means and relaying means is eliminated.

It is necessary to ensure that apexes 16 and 26 of focusing means 12 and relaying means 22 respectively are in intimate contact with surface 52 of medium 14. Preferably apexes 16 and 26 are contacted with a couplant such as glycerol to reduce loss of the ultrasonic wave during its passage from apexes 16 and 26. First transducer 8 is triggered by pulser 6 to generate the ultrasonic wave through medium 14. The second transducer 18 converts the first attenuated ultrasonic wave into the electrical signal. Receiver 20 then analyzes the signal and then displays the signal, shown in FIG. 3, on displaying means such as oscilloscope 38. Time of flight or time interval (t) is defined as the time taken by the first attenuated wave to reach second transducer 18 of relaying means 22 from first transducer 8 of focusing means 12. The first attenuated wave is substantially longitudinal wave 46, shown in FIGS. 2 and 3.

The times of flight ($t_1$), shown in FIG. 3, are recorded for various wedge separations or distances between apex 16 of focusing means 12 and apex 26 of relaying means 22 while the device is maintained at a given orientation. The slope of distance (s) versus time of flight ($t_1$) yields a measured velocity $v_m(ds/dt_1)$ of the first ultrasonic wave transmitted through composite medium 14. As shown in steps 122 and 124, device 1 is rotated along its center to provide several angles of orientation ($\Psi$) to generate a sufficient number of velocity measurements to generate the $v_m$ distribution diagram shown in FIG. 10.

When the device 200 (FIGS. 5, 6) of the alternative preferred embodiment of the present invention is used, the steps of subroutine A, involving taking wave velocity measurements at various wedge separations and at various orientations about a center point, are greatly simplified from an operator's standpoint. Essentially, there is no need to record the orientation of the device with respect to a datum, such as 0°, as the orientation of one of the matched pairs of transducer assemblies, for example T1–R1, can be defined beforehand as representing the 0° datum. There is also no need to rotate the device (step 124 in subroutine A) to obtain velocity measurements at a plurality of orientations between 0° and 180° as that is the purpose for providing the plurality of matched pairs of transducers on device 200. In addition, there is no need to adjust the separation distance between the pairs of transducers, e.g., T1–R1, in order to obtain velocity measurements at two distances along each angle of orientation. Central receiving transducer 7 provides a second measurement distance for each transmitted and received pulse.

The steps employed in using device 200 in its computer-controlled mode will now be discussed in further detail. The transducer assemblies T1–T6, R1–R6 and R7 are brought into contact with the surface 52 of medium 14 (see FIG. 6), and preferably a couplant, as described previously, is employed to provide reduced loss of the ultrasonic wave when transmitted into and received from the medium 14. It is envisioned that a tuning or adjustment step may be required, at least initially, to adjust the ultrasonic pulser/receiver 204, the in-line attenuator 220 coupled to the R7 transducer assembly, and the in-line receiver/amplifier 208, such that usable signals are received on all channels.

Further potentially desirable initial steps would be to input into the data acquisition computer 226 information related to the medium which is to undergo evaluation, such as a description of the composite sheet, possibly by date, time, and production lot, and/or information related to the location on the sheet where the examination will be conducted, and/or and special notes which might later be useful in referencing the results of the evaluation. In addition, prior to making the actual velocity measurements, it may be desirable to select the number of signal repetitions (for signal averaging on the digital oscilloscope 224) such that the waveforms reconstructed from the data are well sampled, smooth, and are displayed at good signal to noise ratios.

Once the initial setup of the device is effected, the procedure for making the velocity measurements involves operating the digital switch 212, which can be effected by a program in computer 226 through line 227, to sequentially connect the ultrasonic pulser 204 to each of the transmitting transducer assemblies T1 through T6, to allow at least one ultrasonic wave to be transmitted into the medium by each transmitter. The digital switch 212 also effectuates a connection between receiver/amplifier 208 and receiver means 210 to receive the signal from the receiving transducer assembly associated with the transmitting transducer assembly which is transmitting the ultrasonic wave at that time.

For each transmitter position, computer 226 acquires and stores a digitized time-averaged digitized waveform signal received at R7 and at the corresponding receiver R1 through R6, through receiving means 210 and digital oscilloscope 224. A time differential or delay between the pulse arrival time at R7 and the pulse arrival time at R1 to R6 is determined for each transmitter position T1 to T6. Wave velocities in the directions T1/R1 through T6/R6 can then be calculated by dividing the distance at which the tip of receiving transducer R7 is spaced from the knife-edge of each of receiving transducers R1–R6, by the above-noted time differential between the pulse arrival times at those positions. It is envisioned that a preferred spacing between the tip of R7 and the knife-edges of R6 will be on the order of 2.0 inches, but in any event, if computer 226 is to be used to perform the velocity calculations, the spacing will be provided as an input to the program. The results of the wave velocity calculations are then used to carry out step 82 shown on the FIG. 7a flowchart. The velocities may be stored in the computer to have the plot called for in step 82 performed as part of a running program, and/or the plot may be displayed on a screen like that shown at 42 of FIG. 4, or a hard copy of a plot like that of FIG. 10 could be generated by an x-y plotter or a commercially available printer 43 (FIG. 4) suitable for use with computer 226.

It can thus be seen that the use of device 200 eliminates the need for an operator to record various orientations and to manipulate the device through the series of orientations, and eliminates the need to set and reset wedge spacings for calculation of a time differential at each orientation. As such, subroutine A of FIG. 8 is streamlined and automated to a great extent when using device 200, although the results obtained are used for the same purpose.

The device 200 can also be employed without a computer 226, but increased operator involvement would be necessary. In such an embodiment, digital switch 212 would be operated manually instead of being under the control of a computer. The received signals from R7 and R1–R6 (sequentially) are displayed on the digital oscilloscope. The operator then must, for each pair of transducers T1/R1 through T6/R6, determine the time differential between the travel times for the ultrasonic waves to reach R7 and R1–R6. This can be done by setting oscilloscope cursors at the leading edge of the displayed pulses from R7 and the receiver R1–R6 currently in use (see "$\Delta t$" in FIG. 5), and setting the oscilloscope to determine and display the time difference between the cursors. The arrival time difference (displayed in microseconds) is then recorded for use in calculating the wave velocity (spacing/time difference). The process is repeated for all six channels and the resulting velocity information is plotted as in FIG. 10, either manually or by entering the information into a separate computer or plotter memory, and having a plot printed out in a known manner.

Figure 11:
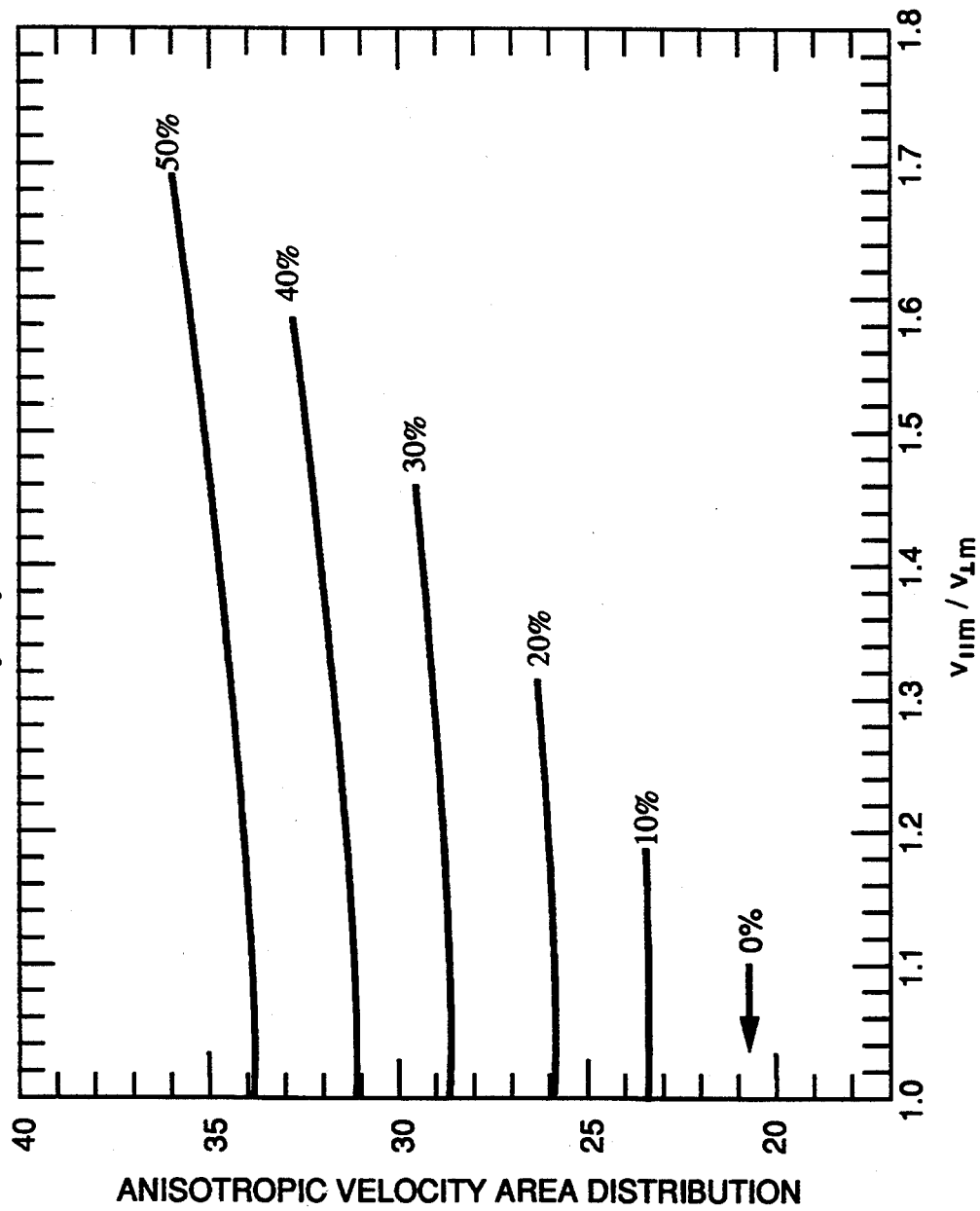
FIG. 11 is a graph of anisotropic velocity area distribution versus ratio of maximum measured velocity ($v_l/m$) to minimum measured velocity ($v_\perp m$) at various fiber percentages present in a fiber reinforced composite medium.

Subroutine B of FIG. 9 provides the steps 130 through 141 necessary for preparing a lookup chart of theoretical normalized area distribution shown in FIG. 12. In order to generate the lookup chart of FIG. 12 it is necessary to know the Young's modulus ($E_f$), Poisson's ratio ($v_f$) and density ($p_f$) of the fiber reinforcement as well as the Young's modulus ($E_{mv}$) and Poisson's ratio ($v_{mv}$) of the matrix material at the frequency of the ultrasonic velocity being transmitted through composite medium 14. It is also necessary to use the chart of FIG. 11 which correlates theoretical anisotropic velocity area distribution with the ratios of maximum measured velocity ($v$l/m) to minimum measured velocity ($v\perp$m) at various fiber percentages. If all the aforestated values are available, the lookup chart of FIG. 12 at different theoretical velocities $v_T$ is prepared by using the formula shown in step 134.

If $E_{mv}$ and $v_{mv}$ are unknown, and if a sample medium of a non-reinforced polymer matrix having the same thickness as composite medium 14 is available, then the velocity ($v_T$) distribution of the first ultrasonic wave, using the aforementioned sample, is determined through subroutine A of FIG. 8, or the variation thereof using device 200. It is desirable to use a sample medium of substantially the same thickness as composite medium 14 because the ultrasonic velocity transmitted through the medium may vary with a change in the thickness of the medium. The velocity ($v_T$) distribution from step 138 is then used in step 134 to prepare the lookup chart of FIG. 12.

If a sample medium of the same thickness as composite medium 14 is not available, then, as disclosed in step 140 of FIG. 9, the fiber weight percentage of composite medium 14 is determined by external means such as burning off the matrix of preweighed composite medium 14 and then weighing the residue comprising the reinforcing fibers. The fiber weight percentage is then used in step 134, in solving Equation (1) and determining ($E_{mv}$) and ($v_{mv}$).

While the embodiment illustrated herein discloses a device for determining the physical attributes of a fiber reinforced composite, the invention is not so limited. The device of the preferred embodiment may be also used for determining the physical attributes of a non-fiber reinforced polymer matrix.

The device of the preferred embodiment may also be used for producing a fiber reinforced polymer sheet of a desired fiber volume fraction and/or a desired fiber orientation by measuring and establishing fiber volume fractions and/or orientations yielding the desired material properties and then periodically comparing the fiber volume fraction present in the sheet being produced with the desired fiber volume fraction data stored in the data storage area of the measurement device of the preferred embodiment. The amount of fiber present in the sheet is then regulated to substantially match the desired fiber volume fraction, and/or the process is controlled to provide the desired fiber orientation. This process can be employed as a process for maintaining quality control over a production run of fiber reinforced polymer sheets.

The present invention will be further understood from the specific examples which follow.

EXAMPLE 1

Material: Discontinuous fiber reinforced composite made of Himont Profax ® polypropylene matrix and glass fiber (0.5 inch length, 16 μm diameter).

Ultrasonic transducers: Krautkramer Branson Aerotech model #PN4539, 0.5 MHz, 0.5 inch diameter, Gamma series having MSWS (miniature size with standard microdot) style connector.

The device of the preferred embodiment of FIG. 4 was placed on the selected surface of the aforementioned composite material and aligned with the marking that corresponded to the angle of orientation of 0° (datum). The ultrasonic wave was transmitted through the composite material and then analyzed. The device was then repositioned to the next marking that corresponded to the next angle of orientation and the process was repeated until the required measurements were obtained.

TABLE I

| Angle of Orientation ($\Psi$) (degrees) | First ultrasonic velocity ($v_m$) (mm/μsec)* | Young's modulus (E) obtained from ultrasonic velocity measurements ($10^6$ psi) | Young's modulus (E) measured by universal tensile machine @ ($10^6$ psi) |
|---|---|---|---|
| 0 | 3.12  3.23 | $E_{22}$ = 1.016 | 1.015 |
|    | 3.03  3.15 | | |
| 30 | 3.03  3.04 | | |
|    | 3.00 | 0.800 | |
| 45 | 3.19  2.97 | | |
|    | 2.90  3.08 | | |
|    | 3.07  3.19 | 0.687 | |
| 60 | 2.84  2.77 | | |
|    | 2.78 | 0.625 | |
| 90 | 2.75  2.70 | | |
|    | 2.80  2.71 | $E_{33}$ = 0.593 | 0.579 |
| 105 | 2.77 | 0.600 | |
| 150 | 3.09 | 0.800 | |
| 165 | 3.11 | 0.942 | |
| 180 | 3.23 | $E_{22}$ = 1.016 | 1.015 |

Glass wt %:
Predicted: 30
Actual: 33**
*Velocity measured as a slope of distance vs time plot. Time measurements were made over wedge separation distances of 4–6 centimeters.
**Glass weight percentage measured by dividing the glass weight (obtained by burning off the matrix at 450° C.) by the total sample weight (matrix + glass). @ Instron Model 1350

Figure 16:
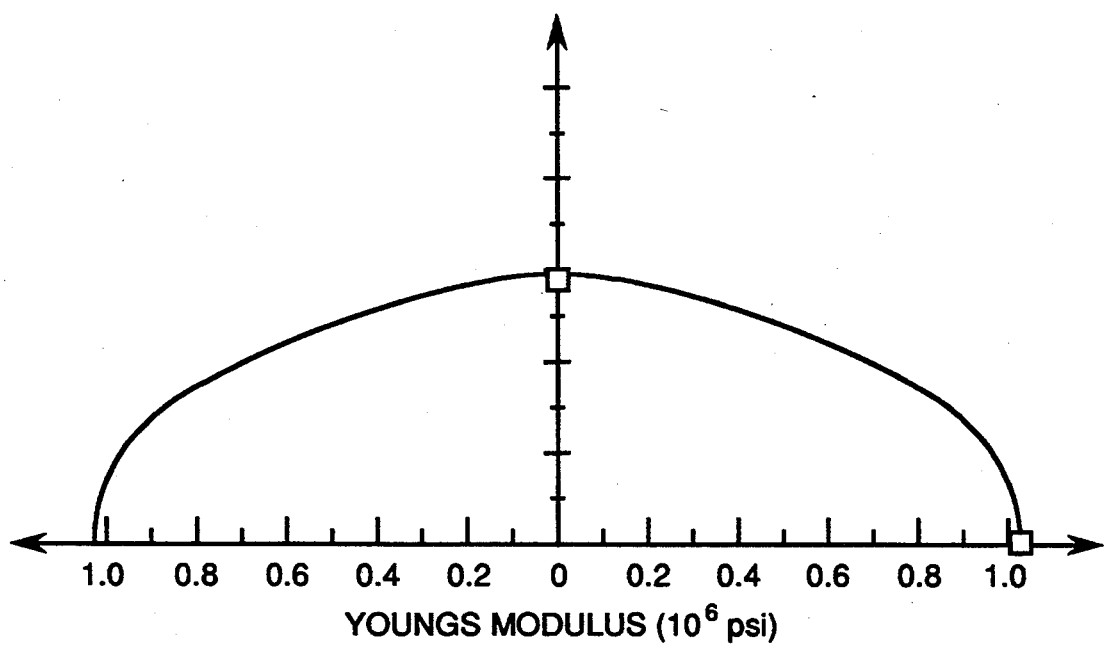
FIG. 16 is a polar graph of the Young's modulus as a function of the angle orientation ($\Psi$) used in Example 1.

FIG. 16 shows the model prediction of the Young's modulus (E) as a function of the angle of orientation ($\Psi$) for Example 1. As shown in Table 1, the Young's modulus measured by the universal tensile machine compares favorably with the Young's modulus obtained through the ultrasonic velocity measurements.

TABLE 2

$$[S] = \begin{bmatrix} \frac{1}{E_{11}} & -\frac{v_{12}}{E_{11}} & -\frac{v_{13}}{E_{11}} & 0 & 0 & 0 \\ -\frac{v_{21}}{E_{22}} & \frac{1}{E_{22}} & -\frac{v_{23}}{E_{22}} & 0 & 0 & 0 \\ -\frac{v_{31}}{E_{33}} & -\frac{v_{32}}{E_{33}} & \frac{1}{E_{33}} & 0 & 0 & 0 \\ 0 & 0 & 0 & \frac{1}{\mu_{23}} & 0 & 0 \\ 0 & 0 & 0 & 0 & \frac{1}{\mu_{13}} & 0 \\ 0 & 0 & 0 & 0 & 0 & \frac{1}{\mu_{12}} \end{bmatrix}$$

v = Poisson's ratio
E = Young's modulus
μ = shear modulus
Compliance constant array = [S], in units of $10^{-6}$ (pounds per square inch)$^{-1}$
$\underline{\epsilon} = [S]\underline{\sigma}$
and where $\epsilon$ (same as $\underline{\epsilon}$) and $\sigma$ (same as $\underline{\sigma}$) are the engineering constants $$\underline{\epsilon} = \begin{bmatrix} \epsilon_1 \\ \epsilon_2 \\ \epsilon_3 \\ \epsilon_4 \\ \epsilon_5 \\ \epsilon_6 \end{bmatrix} \quad \underline{\sigma} = \begin{bmatrix} \sigma_1 \\ \sigma_2 \\ \sigma_3 \\ \sigma_4 \\ \sigma_5 \\ \sigma_6 \end{bmatrix}$$

$\epsilon_1 = \epsilon_{11}$     $\epsilon_2 = \epsilon_{22}$     $\epsilon_3 = \epsilon_{33}$
$\epsilon_4 = 2\epsilon_{23}$     $\epsilon_5 = 2\epsilon_{13}$     $\epsilon_6 = 2\epsilon_{12}$

TABLE 2-continued $\underline{\sigma}_1 = \sigma_{11}$    $\underline{\sigma}_2 = \sigma_{22}$    $\underline{\sigma}_3 = \sigma_{33}$
$\underline{\sigma}_4 = \sigma_{23}$    $\underline{\sigma}_5 = \sigma_{13}$    $\underline{\sigma}_6 = \sigma_{12}$ where 0° direction is defined as along 2-axis, and 90° direction is along 3-axis.

$$[S] = \begin{bmatrix} 2.451 & -0.314 & -0.703 & 0 & 0 & 0 \\ -0.314 & 0.984 & -0.385 & 0 & 0 & 0 \\ -0.703 & -0.385 & 1.685 & 0 & 0 & 0 \\ 0 & 0 & 0 & 3.912 & 0 & 0 \\ 0 & 0 & 0 & 0 & 8.293 & 0 \\ 0 & 0 & 0 & 0 & 0 & 8.176 \end{bmatrix}$$ (2 axis is dominant)

Table 2 shows the compliance constants array, [S], in terms of Poisson's ratio ($\nu$), Young's modulus (E) and shear modulus ($\mu$), and in terms of numerical values obtained from the model output for Example 1 where the 0° direction is defined as along the 2-axis, and the 90° direction is defined as along the 3-axis. From this array, the predicted Young's modulus in the 0° direction is $E_{22}$ $1/0.984 = 1.016 \times 10^6$ psi. Likewise, the predicted Young's modulus in the 90° direction is $E_{33} = 1/1.685 = 0.593 \times 10^6$ psi.

EXAMPLE 2

Material: Discontinuous fiber reinforced composite made of Lexan ® polycarbonate matrix and glass fiber (0.5 inch length, 16 μm diameter).

Ultrasonic Transducers: Krautkramer Branson Aerotech model #PN4539, 0.5 MHz, 0.5 inch diameter, Gamma series, having MSWS (miniature size with standard microdot) style connector.

The same measurement procedure as the one described in Example 1 was followed in Example 2.

TABLE 4

$$[S] = \begin{bmatrix} \frac{1}{E_{11}} & -\frac{\nu_{12}}{E_{11}} & -\frac{\nu_{13}}{E_{11}} & 0 & 0 & 0 \\ -\frac{\nu_{21}}{E_{22}} & \frac{1}{E_{22}} & -\frac{\nu_{23}}{E_{22}} & 0 & 0 & 0 \\ -\frac{\nu_{31}}{E_{33}} & -\frac{\nu_{32}}{E_{33}} & \frac{1}{E_{33}} & 0 & 0 & 0 \\ 0 & 0 & 0 & \frac{1}{\mu_{23}} & 0 & 0 \\ 0 & 0 & 0 & 0 & \frac{1}{\mu_{13}} & 0 \\ 0 & 0 & 0 & 0 & 0 & \frac{1}{\mu_{12}} \end{bmatrix}$$

Compliance constant array = [S], in units of $10^{-6}$ (pounds per square inch)$^{-1}$
where $\epsilon = [S]\sigma$, 0° direction is defined to be along 2-axis, and 90° direction is defined to be along 3-axis.
For $e = 0$, $$[S] = \begin{bmatrix} 1.738 & -0.318 & -0.318 & 0 & 0 & 0 \\ -0.318 & 0.925 & -0.302 & 0 & 0 & 0 \\ -0.318 & -0.302 & 0.925 & 0 & 0 & 0 \\ 0 & 0 & 0 & 2.456 & 0 & 0 \\ 0 & 0 & 0 & 0 & 5.812 & 0 \\ 0 & 0 & 0 & 0 & 0 & 5.812 \end{bmatrix}$$

and for $e = 0.5$ $$[S] = \begin{bmatrix} 1.738 & -0.304 & -0.332 & 0 & 0 & 0 \\ -0.304 & 0.900 & -0.302 & 0 & 0 & 0 \\ -0.332 & -0.302 & 0.951 & 0 & 0 & 0 \\ 0 & 0 & 0 & 2.458 & 0 & 0 \\ 0 & 0 & 0 & 0 & 5.818 & 0 \\ 0 & 0 & 0 & 0 & 0 & 5.806 \end{bmatrix}$$

TABLE 3

| Angle of orientation (Ψ) Angle (degrees) | First ultrasonic velocity ($v_m$) (mm/μsec)* | Young's modulus obtained from ultrasonic velocity measurements ($10^6$ psi) | | Young's modulus (E) measured by universal tensile machine @ ($10^5$ psi) |
|---|---|---|---|---|
| | | Assuming an isotropic composite medium, e** = 0 | Best fit for anisotropic composite medium, e** = 0.5 | |
| 0 | 3.00 | 1.08 | 1.11 | 1.080 |
| 90 | 2.93 | 1.08 | 1.05 | |
| 45 | 2.89, 3.08 | 1.08 | 1.08 | |

| Glass Wt % | | |
|---|---|---|
| Predicted | | Actual*** |
| Assuming isotropic composite medium, e = 0 | Best fit for anisotropic composite medium, e = 5 | |
| 34 | 34 | 32.1 |

*Velocity measured as a slope of distance vs time plot. Time measurements were made over wedge separation distances of 4–6 cm.
**e = eccentricity of elliptical distribution of Equation 21.
***Glass weight percentage measured by dividing the glass weight (obtained by burning off the matrix at 450° C.) by the total sample weight (matrix + glass).

Figure 17:
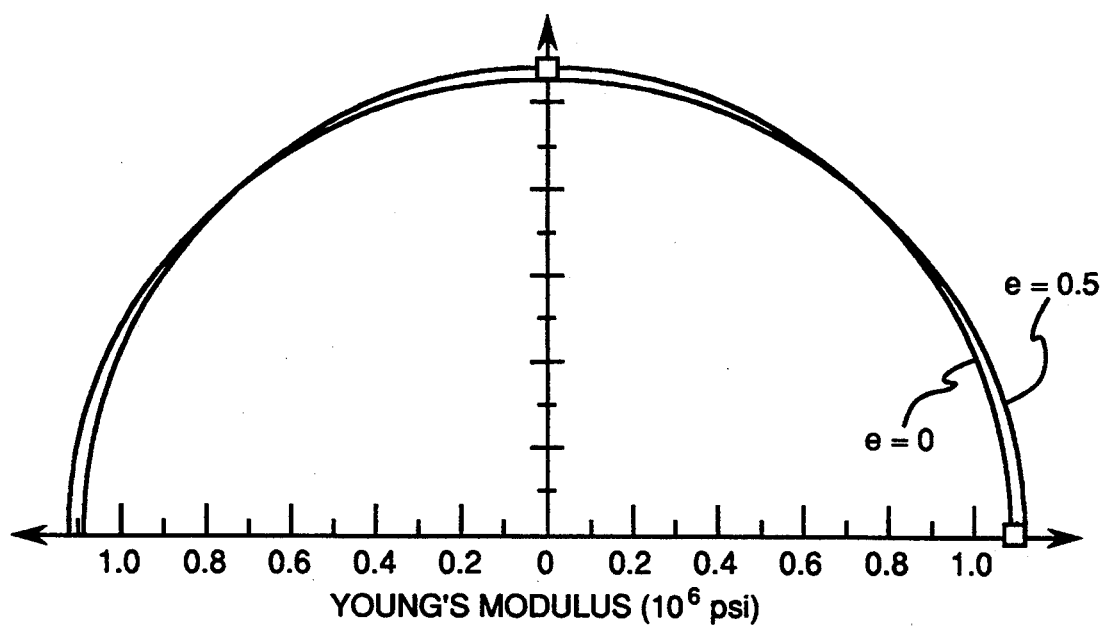
FIG. 17 is a polar chart of the Young's modulus as a function of the angle orientation ($\Psi$) used in Example 2 at two eccentricities.

FIG. 17 plots the two predictions of the Young's modulus as a function of the angle of orientation (Ψ) where the prediction for the isotropic composite medium (e=0) is a semi-circle and the prediction for the best fit for the anisotropic composite medium (e=0.5) is a semi-ellipse. As shown in Table 3, the Young's modulus measured by the Universal tensile machine compares favorably with that obtained from the ultrasonic velocity measurements both in units of $10^6$ (pounds per square inch)$^{-1}$.

Table 4 shows the same compliance constants array in terms of $\nu$, E, and $\mu$ as was shown in Table 2. Again, the corresponding numerical values are shown in the array for e=0 and e=0.5, where the 0° direction is defined as along the 2-axis and the 90° direction is defined as along the 3-axis. From this array, the predicted Young's modulus in the 0° direction for e=0 and e=0.5 is $E_{22} = 1/0.925 = 1.08 \times 10^6$ psi and $E_{22} = 1/0.900 = 1.11 \times 10^6$ psi, respectively. Likewise, the predicted Young's modulus in the 90° direction for $e=0$ and $e=0.5$ is $E_{33}=1/0.925=1.08\times 10^6$ psi and $E_{33}=1/0.951=1.05\times 10^6$ psi, respectively.

Table 3 tabulates the results found using the compliance constants array and compares these predictions to the Young's modulus measured by the universal tensile machine. The predictions based on the isotropic fiber orientation distribution ($e=0$, fibers having no preferred orientation) fit well with the Young's modulus measured by the universal tensile machine.

Figure 15:
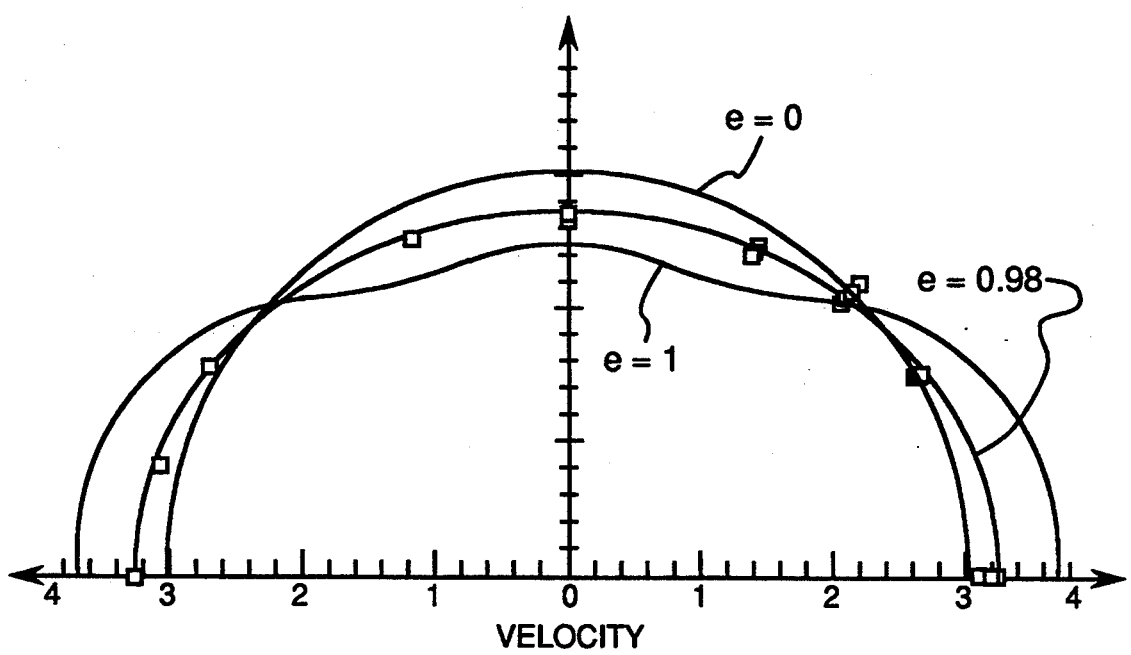
FIG. 15 is a graphical comparison of the theoretical velocity distribution diagram with the measured velocity distribution diagram for determining eccentricity of an elliptical distribution function.
Figure 18:
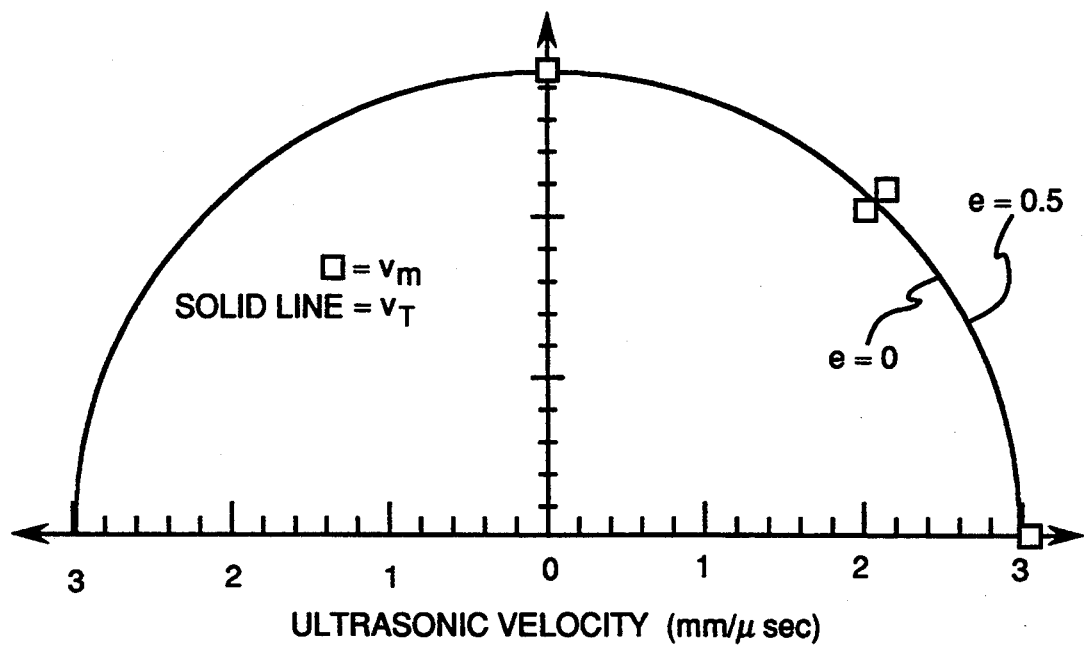
FIG. 18 is a polar chart of the measured ($v_m$) and theoretical ($v_T$) ultrasonic velocities.

FIG. 18 shows the polar plot of the measured ($v_m$) and theoretical ($v_T$) ultrasonic velocities as a function of angle $\Psi$ for fiber orientations defined as $e=0$ and $e=0.5$. Reference is also made to FIG. 15. These predictions essentially fall on the same line. The squares shown in FIG. 18 are the measured ultrasonic velocities ($v_m$) and the solid line represents ($v_T$) as determined by processing means 4 of the preferred embodiment. The differences between the two predictions are more easily seen in the FIG. 17 plot of the Young's modulus.

Figure 19:
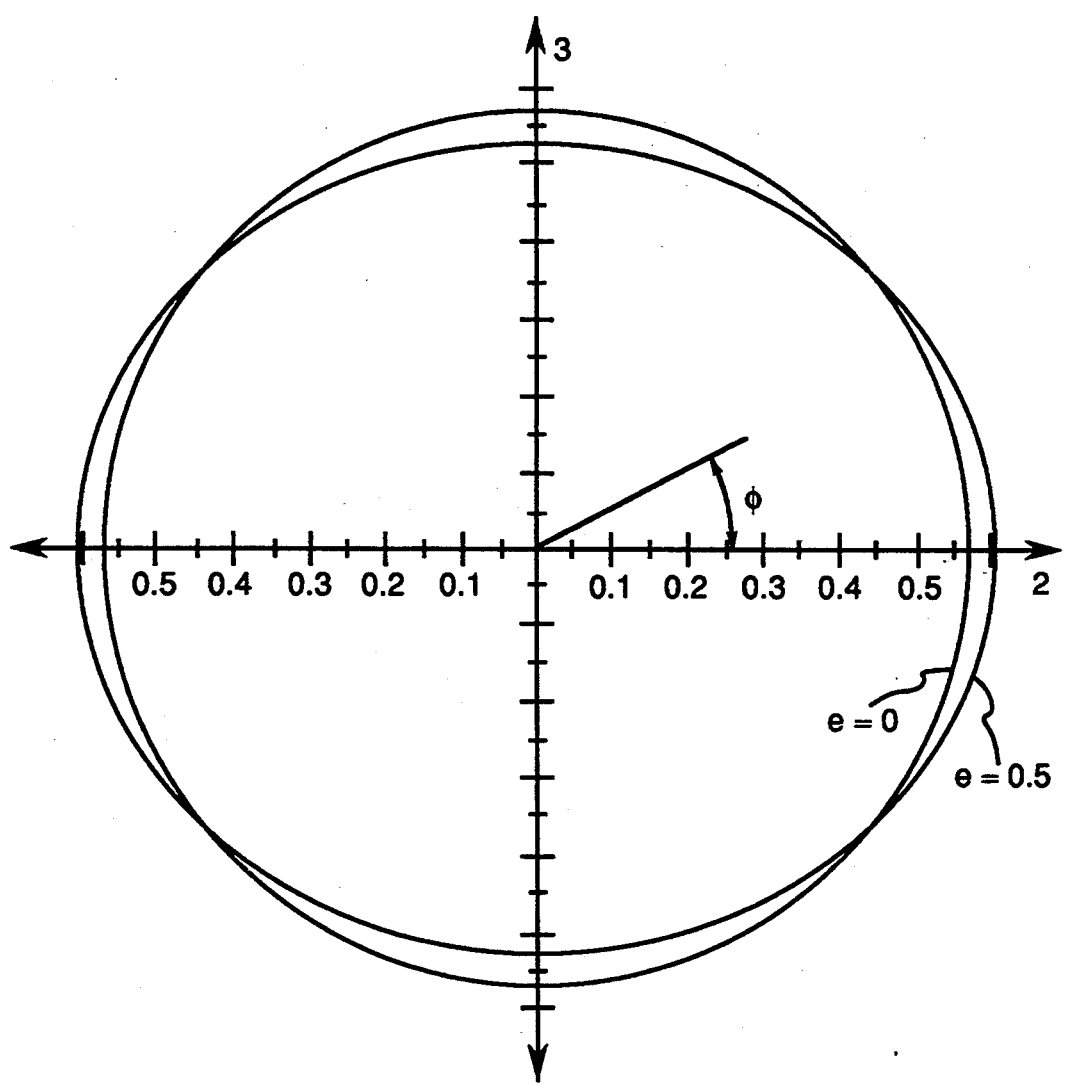
FIG. 19 is the two dimensional (planar) elliptical fiber distribution at two different eccentricities.

FIG. 19 shows the 2-D planar distribution at two different eccentricities of $e=0$ and $e=0.5$. The fiber orientation distribution is represented by the eccentricity (e) of the elliptical distribution of Equation (12). The distribution defined as $e=0$, is for randomly distributed fibers, i.e., there is an equal chance that a fiber will be oriented at any angle $\phi$. Thus, the distribution is a circle. The distribution defined as $e=0.5$ is for fibers with a preferred orientation in the 0° direction (labeled here as the 2-axis), i.e., there is a greater chance that a fiber will be oriented along the 2-axis than the 3-axis. Thus, the distribution is an ellipse with the major axis along the 2-axis.

What is claimed is:

1. A measurement device for determining the in-plane physical attributes of an anisotropic lossy medium, comprising:
   (I) wave generator means for generating an ultrasonic sound wave;
   (II) focusing means having an impedance substantially matched to that of said medium wherein said focusing means focuses and transmits said ultrasonic wave through said medium;
   (III) wave converter means for converting into an electrical signal a first attenuated wave received through said medium;
   (IV) relaying means having an impedance substantially matched to that of said medium wherein said relaying means relays said first attenuated wave to said converter means; and
   (V) processing means for transforming said signal into a record of said attributes;
   said processing means (V) comprising:
   (A) means for determining velocities of said first attenuated ultrasonic wave transmitted through said medium at various angles of orientation ($\Psi$) within said medium; and
   (B) means for determining said physical attributes of said medium;
   said determining means (B) further comprising:
   means for plotting a measured anisotropic velocity (v) distribution diagram as a function of said angles of orientation ($\Psi$) and said determined velocities;
   means for screening said measured anisotropic velocity distribution diagram to determine $v_{maximum}$, $\Psi_{maximum}$, $v_{minimum}$ and $\Psi_{minimum}$;
   means for computing a measured degree of anisotropy from said $v_{minimum}$/said $v_{maximum}$;
   means for computing an area of said measured anisotropic velocity distribution diagram from $$\int_0^{2\pi} [v(\psi)]^2 d\psi/2$$

where $\pi$ equals 3.14159 . . .;
   means for retrieving a lookup chart for said measured degree of anisotropy stored in a data storage area of said processing means wherein said lookup chart provides measured normalized area distribution;
   means for determining an area of isotropic velocity distribution from a ratio of said measured anisotropic velocity distribution to said measured normalized area distribution;
   means for determining a volume fraction of reinforcement in said medium, the reinforcement corresponding to weight percentage in said medium, said means for determining a volume fraction of reinforcement employing a functional relationship between said volume fraction and a theoretical area of isotropic velocity distribution or data representative of said functional relationship;
   means for comparing and matching a theoretical velocity distribution diagram with said measured velocity distribution diagram to determine the eccentricity of an elliptical distribution function;
   means for determining $C_{ijkl}$ tensors from said elliptical distribution function; and
   means for calculating said physical attributes of said medium from said $C_{ijkl}$ tensors.

2. The device according to claim 1 further comprising amplifier means for providing a gain to said signal.

3. The device according to claim 1 further comprising a support member having a lower propagation velocity than said medium wherein said focusing means and said relaying means are secured to said support member.

4. The device according to claim 3 further comprising sliding means disposed on said support member to provide slidable adjustment to said focusing means and to said relaying means such that distance between said focusing and relaying means can be varied.

5. The device according to claim 4 wherein said focusing means and said relaying means each have a cuneate shape wherein an apex of said cuneate shape is downwardly disposed from said focusing means and said relaying means and wherein a base of said cuneate shape is adjacent to said support member such that each apex of said focusing and relaying means contacts a surface of said medium.

6. The device according to claim 1 wherein said wave generator means comprises:
   a first electroacoustic transducer mounted on said focusing means; and
   an adjustable electrical supply means for supplying variable power to said first electroacoustic transducer such that said first electroacoustic transducer is capable of generating said ultrasonic sound wave of a desired frequency and power.

7. The device according to claim 6 wherein said converter means comprises:
   a second electroacoustic transducer mounted on said relaying means; and
   a receiver means for receiving said electrical signal for further analysis.

8. The device according to claim 7 wherein said first electroacoustic transducer and said second electroacoustic transducer have substantially same piezoelectric constant.

9. The device according to claim 5 wherein said means for determining said velocities comprises:
   means for recording an angle of said angles of orientation ($\Psi$) of said device with respect to a datum;
   means for determining a time interval required at each of said angles of orientation ($\Psi$) for said electrical signal to arrive from said apex of said focusing means to said apex of said relaying means; and
   means for pivoting said device along a center point to place said device at a series of said angles of orientation ($\Psi$) for obtaining a corresponding series of time intervals.

10. The device according to claim 1 further comprising means for displaying said physical attributes of said medium.

11. The device according to claim 10 further comprising means for imprinting a character representing an orientation of said wave generator means on said medium.

12. The device according to claim 1 wherein said focusing means comprises a plurality of transmitting transducer assemblies secured to a mounting means at various angles of orientation relative to a center point of said mounting means, and said relaying means comprises a corresponding plurality of receiving transducer assemblies, each of said plurality of transmitting transducer assemblies having a receiving transducer assembly associated therewith and positioned at a diametrically opposed location about said center point, so as to form a plurality of transmitter/receiver pairs.

13. The device according to claim 12 further comprising a central relaying means in the form of a central receiving transducer assembly, said central relaying means being disposed at a common crossing point of a straight line extending between each pair of said plurality of transmitter/receiver pairs.

14. The device according to claim 13 wherein said mounting means has a higher impedance than said anisotropic Lossy medium.

15. The device according to claim 13 wherein each of said plurality of transmitting transducer assemblies and each of said plurality of receiving transducer assemblies has a focusing wedge means having a cuneate shape extending away from said mounting means and forming a knife-edge apex at a lower end thereof.

16. The device according to claim 15 wherein said central transducer assembly has a conically shaped focusing means forming a point contact.

17. The device according to claim 16 wherein each said knife-edge apex of each of said focusing wedge means and said point contact of said conically shaped focusing means all lie in a single plane.

18. The device according to claim 12 wherein a transducer element in each of said plurality of transmitting transducer assemblies and in each of said receiving transducer assemblies is cylindrically focused.

19. The device according to claim 13 wherein a transducer element in said central receiving transducer assembly is spherically focused.

20. The device according to claim 12 further comprising switch means for successively selecting a transmitter/receiver pair.

21. The device according to claim 20 further comprising a computer and wherein said switch means is a digital switch means controlled by said computer.

22. The device according to claim 13 wherein said means for determining velocities of said ultrasonic wave includes means for measuring a time differential between the arrival of said first attenuated wave at the central receiving transducer assembly and at a receiving transducer assembly diametrically opposed to a transmitting transducer assembly which has transmitted the ultrasonic wave.

23. A method of determining the in-plane physical attributes of an anisotropic medium comprising:
   (a) selecting a surface area of said medium and placing a measurement device on said surface;
   (b) recording an angle of orientation ($\Psi$) of a velocity measurement to be taken by said device with respect to a datum;
   (c) transmitting an ultrasonic wave through said medium;
   (d) determining a time interval required at said orientation for a signal corresponding to a first attenuated ultrasonic wave to travel between a first predetermined point and a second predetermined point;
   (e) repeating steps (b)–(d) above at a plurality of angles of orientation ($\Psi$);
   (f) plotting a measured anisotropic velocity distribution diagram as a function of said plurality of angles of orientation ($\Psi$) wherein a measured velocity (v) at each angle of orientation ($\Psi$) is determined by dividing the distance between said first and second predetermined points by the time interval determined at each said angle of orientation ($\Psi$);
   (g) screening said measured anisotropic velocity distribution diagram to determine $v_{maximum}$, $\Psi_{maximum}$, $v_{minimum}$ and $\Psi_{minimum}$;
   (h) computing a measured degree of anisotropy from said $v_{minimum}$/said $v_{maximum}$;
   (i) computing an area of said measured anisotropic velocity distribution diagram from $$\int_0^{2\pi} [v(\psi)]^2 d\psi/2$$

where $\pi$ equals 3.14159 . . .;
   (j) retrieving a lookup chart for said measured degree of anisotropy stored in a data storage area of said processing means wherein said lookup chart provides measured normalized area distribution;
   (k) determining an area of isotropic velocity distribution from a ratio of said measured anisotropic velocity distribution to said measured normalized area distribution;
   (l) obtaining a measured volume fraction of reinforcement present in said medium, the reinforcement corresponding to weight percentage in said medium by employing a functional relationship between said volume fraction and a theoretical area of isotropic velocity distribution or employing data representative of said functional relationship, wherein the ratio-determined area of step (k) is used as a pertinent value for a theoretical area of isotropic velocity distribution;
   (m) comparing and matching a theoretical velocity distribution diagram with said measured velocity distribution diagram to determine an eccentricity of an elliptical distribution function;

(n) determining $C_{ijkl}$ tensors from said elliptical distribution function;

(o) calculating said physical attributes of said medium from said $C_{ijkl}$ tensors.

24. The method according to claim 23 comprising the further step of:

(p) displaying said attributes.

25. The method according to claim 24 comprising the further steps of:

(q) determining the amplitude of said first attenuated ultrasonic wave, and (r) matching said amplitude with a predetermined acceptable range, wherein steps (q) and (r) are performed before step (d) is performed.

26. The method according to claim 23 wherein said attributes are Young's modulus, shear modulus and Poisson's ratio for said medium in x, y and z directions.

* * * * *